(12) United States Patent
Milad et al.

(10) Patent No.: US 9,271,718 B2
(45) Date of Patent: Mar. 1, 2016

(54) SUTURING AND LIGATING METHOD

(75) Inventors: Magdy P. Milad, Chicago, IL (US); Pari Shimoyama, Ann Arbor, MI (US); Shigeru Omori, Hadano (JP); Deanna Hirzel, Chelsea, MI (US)

(73) Assignee: Karl Storz GmbH & Co. KG, Tuttlingen (DE)

( * ) Notice: Subject to any disclaimer, the term of this patent is extended or adjusted under 35 U.S.C. 154(b) by 1258 days.

(21) Appl. No.: 12/543,102

(22) Filed: Aug. 18, 2009

(65) Prior Publication Data
US 2011/0046643 A1 Feb. 24, 2011

(51) Int. Cl.
*A61B 17/04* (2006.01)
*A61B 17/062* (2006.01)

(52) U.S. Cl.
CPC ......... *A61B 17/0469* (2013.01); *A61B 17/0491* (2013.01); *A61B 17/062* (2013.01)

(58) Field of Classification Search
CPC ........... A61B 17/0469; A61B 17/0491; A61B 17/062; A61B 2017/0474; A61B 2017/0475
USPC .................. 606/139, 144, 148; 112/155, 156
See application file for complete search history.

(56) References Cited

U.S. PATENT DOCUMENTS

| | | | | |
|---|---|---|---|---|
| 5,234,443 A * | 8/1993 | Phan et al. | | 606/148 |
| 5,336,230 A * | 8/1994 | Leichtling et al. | | 606/148 |
| 5,403,330 A * | 4/1995 | Tuason | | 606/148 |
| 5,405,352 A * | 4/1995 | Weston | | 606/148 |
| 5,437,682 A * | 8/1995 | Grice et al. | | 606/148 |
| 5,454,834 A * | 10/1995 | Boebel et al. | | 606/228 |
| 5,643,293 A * | 7/1997 | Kogasaka et al. | | 606/148 |
| 5,681,331 A * | 10/1997 | de la Torre et al. | | 606/148 |
| 5,702,407 A * | 12/1997 | Kaji | | 606/139 |
| 6,853,879 B2 | 2/2005 | Sunaoshi | | |
| 2005/0228406 A1 * | 10/2005 | Bose | | 606/144 |
| 2008/0039256 A1 * | 2/2008 | Jinno et al. | | 474/148 |
| 2009/0228025 A1 * | 9/2009 | Benson | | 606/144 |

* cited by examiner

*Primary Examiner* — Alexander Orkin
(74) *Attorney, Agent, or Firm* — Whitmyer IP Group LLC

(57) ABSTRACT

In a suturing and ligating method, a suture strand is wound around a gripper a predetermined number of times by turning a proximal end portion of a curved needle with a rolling mechanism. The gripper then grips the portion of the suture strand, which has not been inserted into the tissue. The gripper is then withdrawn through loops of the suture strand, which are wound around the gripper. The distal-end working unit and the gripper are then moved relatively to each other in order to form a knot across the incision.

8 Claims, 41 Drawing Sheets

SUTURING AND LIGATING METHOD

BACKGROUND OF THE INVENTION

1. Field of the Invention

The present invention relates to an intracoelomic suturing and ligating method for suturing and ligating a body tissue using two manipulators inside a body cavity.

2. Description of the Related Art

According to endoscopic surgery (also called laparoscopic surgery), it is customary to form a plurality of incisions on the body surface of a patient, insert trocars (tubular instruments) respectively into the incisions to define forceps instrument passage ports, and introduce tip ends of forceps instruments including shafts through the respective trocars into the body cavity in order to perform a surgical operation on the affected body part. Working units, such as a gripper for gripping a living tissue, scissors, an electrosurgical knife blade, etc., are mounted onto tip ends of such forceps instruments.

An endoscopic surgical operation performed by means of the forceps instruments requires a surgeon to be trained in advance, because the working space within the body cavity is small. Further, the forceps instruments need to be operated using the trocars as fulcrums. Since conventional forceps instruments that have been used heretofore do not have joints in the working unit at the distal end thereof, such forceps instruments tend to have a small degree of freedom, and the working unit can be operated only on an extension of the shaft. Therefore, cases that can be handled in accordance with the usual training practice for endoscopic surgery are confined to a certain range. Moreover, a surgeon needs to be trained and have a considerably high level of skill in order to perform endoscopic surgery on other cases that do not fall within the limited range.

Attempts have been made to improve conventional forceps instruments, so as to develop a forceps instrument including a plurality of joints in the working unit thereof (see, for example, U.S. Pat. No. 6,853,879). Such a forceps instrument, which also is referred to as a manipulator, is free of the limitations and difficulties of conventional forceps instruments, can be operated easily, and can be applied to a wide variety of surgical cases. It is expected that the developed forceps instrument will be applied to techniques requiring intricate manipulative actions within small spaces, for example.

In particular, it is preferable for a suturing and ligating process to be facilitated within limited spaces inside of a body cavity, which heretofore has been difficult to perform.

SUMMARY OF THE INVENTION

It is an object of the present invention to provide an intracoelomic suturing and ligating method, for enabling suturing and ligating of body tissues to be performed easily within a limited space inside of a body cavity.

According to the present invention, a suturing and ligating method is provided, which is to be performed inside a body cavity within a living body, using a first manipulator which has a first distal-end working unit including a rolling mechanism and a first opening and closing mechanism, and a second manipulator which has a second distal-end working unit including a second opening and closing mechanism. The method comprises a needle piercing step of inserting a needle of a suture-needle assembly through a tissue in the body cavity while leaving a portion of a suture strand of the suture-needle assembly uninserted in the tissue, a needle gripping step of gripping the needle with the first opening and closing mechanism, a winding step of winding the suture strand around the second distal-end working unit a predetermined number of times, at least once, by turning a proximal end portion of the needle with the rolling mechanism, a suture strand gripping step of gripping the portion of the suture strand, which is not inserted into the tissue, with the second opening and closing mechanism, a pulling step of pulling an end portion of the suture strand through loops of the suture strand, which are wound around the second distal-end working unit, and a tightening step of forming a knot by moving the first distal-end working unit and the second distal-end working unit in opposite directions from each other.

In the winding step, the suture strand can easily be wound around the second distal-end working unit by changing the orientation of the needle with the rolling mechanism. At this time, only the first distal-end working unit of the first manipulator is swung by the rolling mechanism, and the second manipulator is swung while the first distal-end working unit is swung or remains at rest. Since the first distal-end working unit and the second manipulator are required to move by small distances, they are applicable to use in limited regions within the body cavity. Furthermore, the first manipulator basically is required to operate about one axis by orienting the rolling mechanism alternately to a first rolling direction and a second rolling direction. Therefore, it is easy to train the operator to use the first manipulator. The term "manipulator" as used herein is interpreted broadly enough to encompass a forceps or the like.

The winding step may further comprise a first sub-step of winding the suture strand around the second distal-end working unit a predetermined number of times by turning the proximal end portion of the needle toward a first rolling direction with the rolling mechanism, and a second sub-step of winding the suture strand further around the second distal-end working unit by turning the proximal end portion of the needle with the rolling mechanism, in the opposite direction relative to the first rolling direction. The first sub-step and the second sub-step may be performed at least once.

Positions of the first distal-end working unit and the second distal-end working unit may be juxtaposed in lateral directions, and the first rolling direction and the second rolling direction may be perpendicular to such lateral directions. If the first rolling direction and the second rolling direction are perpendicular to the lateral directions, then the first distal-end working unit moves more greatly than the second distal-end working unit, allowing the suture strand to be wound easily around the second distal-end working unit.

The first distal-end working unit may include a tilting mechanism. Further, at least the winding step may comprise a step of tilting the first distal-end working unit with the tilting mechanism, in a direction from a central axis of the shaft of the first manipulator toward the second distal-end working unit. With the first distal-end working unit being tilted toward the second distal-end working unit, the first distal-end working unit and the second distal-end working unit are close to each other, thereby allowing surgical procedures to be performed with ease.

At least the winding step may comprise a step of leaving the second opening and closing mechanism closed. With the second opening and closing mechanism being closed when the suture strand is to be wound, the suture strand can easily be wound around the second distal-end working unit without becoming entangled within the second opening and closing mechanism.

The first manipulator may include a rotary input unit, which is manually rotatable clockwise and counterclockwise from the initial position, and the rolling mechanism is capable of rolling the first distal-end working unit in response to manual rotation of the rotary input unit. The rotary input unit, which controls the rolling mechanism of the first distal-end working unit, allows the operator to operate the first manipulator intuitively through a simple process.

The needle may comprise a curved needle.

The winding step may further comprise a step of turning the proximal end portion with the rolling mechanism through an angle ranging from 90° to 200°.

According to the present invention, a suturing and ligating method also is provided, which is to be performed inside a body cavity within a living body, using a first manipulator which has a first distal-end working unit including a tilting mechanism and a first opening and closing mechanism, and a second manipulator which has a second distal-end working unit including a second opening and closing mechanism. The method comprises a needle piercing step of inserting a needle of a suture-needle assembly through a tissue in the body cavity while leaving a portion of a suture strand of the suture-needle assembly uninserted in the tissue, a needle gripping step of gripping the needle or the suture strand, which is inserted through the living body, with the second opening and closing mechanism, a winding step of winding the suture strand around the first distal-end working unit a predetermined number of times, at least once, by turning the first distal-end working unit with the tilting mechanism, a suture strand gripping step of gripping the portion of the suture strand that is not inserted into the tissue with the first opening and closing mechanism, a pulling step of pulling the portion of the suture strand through loops of the suture strand, which are wound around the first distal-end working unit, and a tightening step of forming a knot by moving the first distal-end working unit and the second distal-end working unit in opposite directions from each other.

In the winding step, the suture strand can easily be wound around the first distal-end working unit by changing the orientation of the first distal-end working unit with the tilting mechanism. At this time, only the first distal-end working unit is tilted by the tilting mechanism, and the second manipulator is swung while the first distal-end working unit is swung or remains at rest. Since the first distal-end working unit and the second manipulator are required to move by small distances, they are applicable to use in limited regions within the body cavity. Furthermore, the first manipulator basically is required to operate about one axis by orienting the tilting mechanism alternately to first and second tilting directions. The term "manipulator" as used herein is interpreted broadly enough to encompass a forceps or the like.

The winding step may further comprise a first sub-step of winding the suture strand around the first distal-end working unit a predetermined number of times by tilting the first distal-end working unit toward a first tilting direction with the tilting mechanism, and a second sub-step of winding the suture strand further around the first distal-end working unit by tilting the first distal-end working unit to a second tilting direction with the tilting mechanism. The first sub-step and the second sub-step may be performed at least once.

Positions of the first distal-end working unit and the second distal-end working unit may be positioned laterally. The first tilting direction may be any one of such lateral directions, whereas the second tilting direction may be another one of such lateral directions.

Alternatively, the positions of the first distal-end working unit and the second distal-end working unit may be positioned laterally. In this case, the first tilting direction may be any one of vertical directions, which are perpendicular to the lateral directions and the depthwise directions, whereas the second tilting direction may be another one of such vertical directions.

At least the winding step may comprise a step of leaving the first opening and closing mechanism closed. With the first opening and closing mechanism being closed when the suture strand is to be wound, the suture strand can easily be wound around the first distal-end working unit without becoming entangled within the first opening and closing mechanism.

The first manipulator may further include a pair of pushing input units, which are manually operated and laterally spaced from each other as viewed from the operator of the first manipulator and the second manipulator, wherein the tilting mechanism is capable of tilting the first distal-end working unit in response to operation of the pushing input units. The pushing input units for controlling the tilting mechanism of the first distal-end working unit allow the operator to operate by his or her thumb the first manipulator intuitively through a simple process.

The winding step may further comprise a step of tilting the first distal-end working unit with the tilting mechanism through an angle ranging from 60° to 90°.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Intracoelomic suturing and ligating methods according to preferred embodiments of the present invention will be described below with reference to FIGS. 1 through 41. The intracoelomic suturing and ligating methods according to the preferred embodiments of the present invention are carried out using at least two manipulators. First, a medical manipulator 10 (hereinafter referred to as "manipulator 10"), which constitutes a first manipulator for use in the intracoelomic suturing and ligating methods according to the preferred embodiments of the present invention, will be described below.

Figure 1:
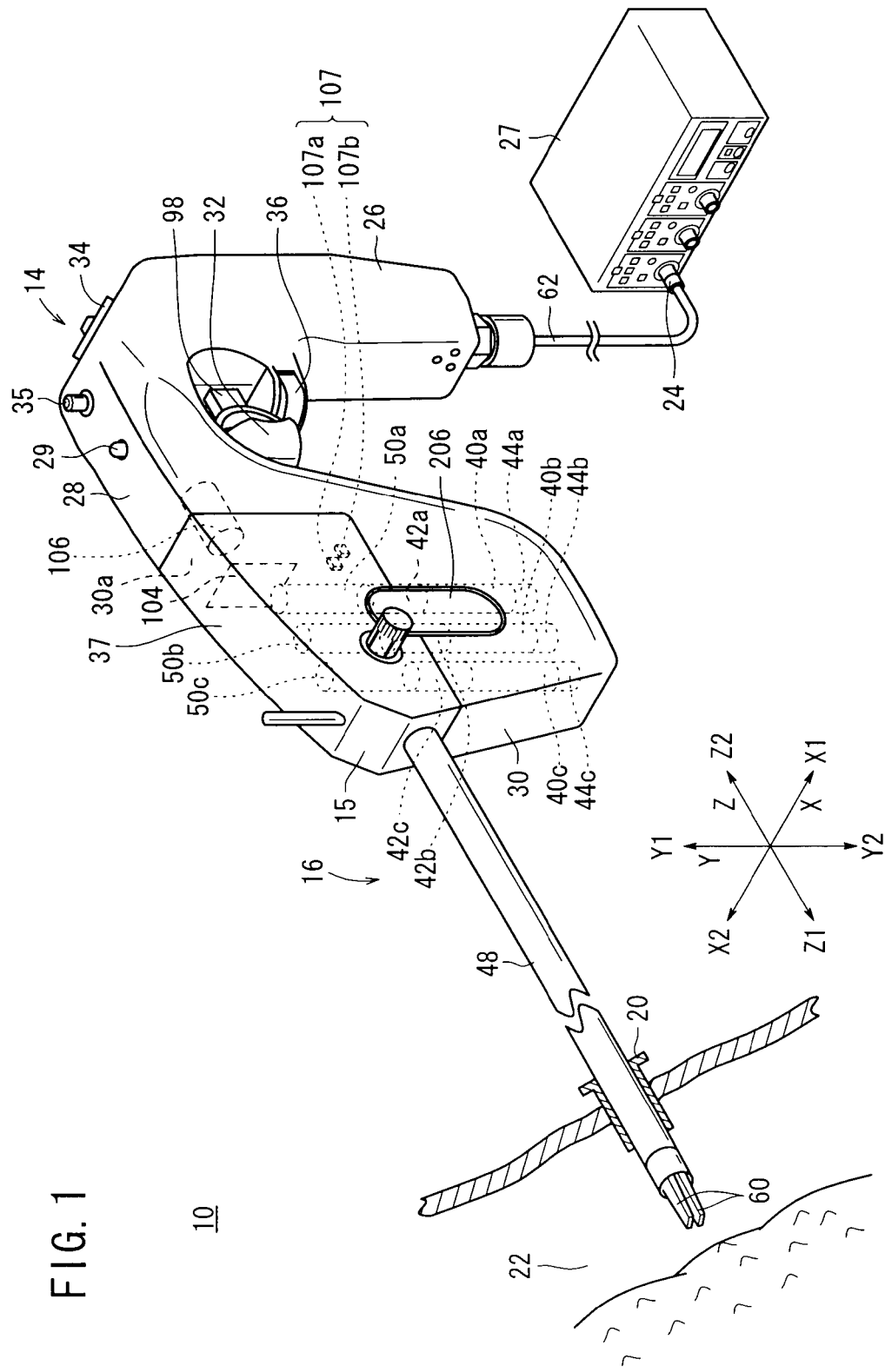
FIG. 1 is a perspective view of a medical manipulator, which is used in the present invention.
Figure 2:
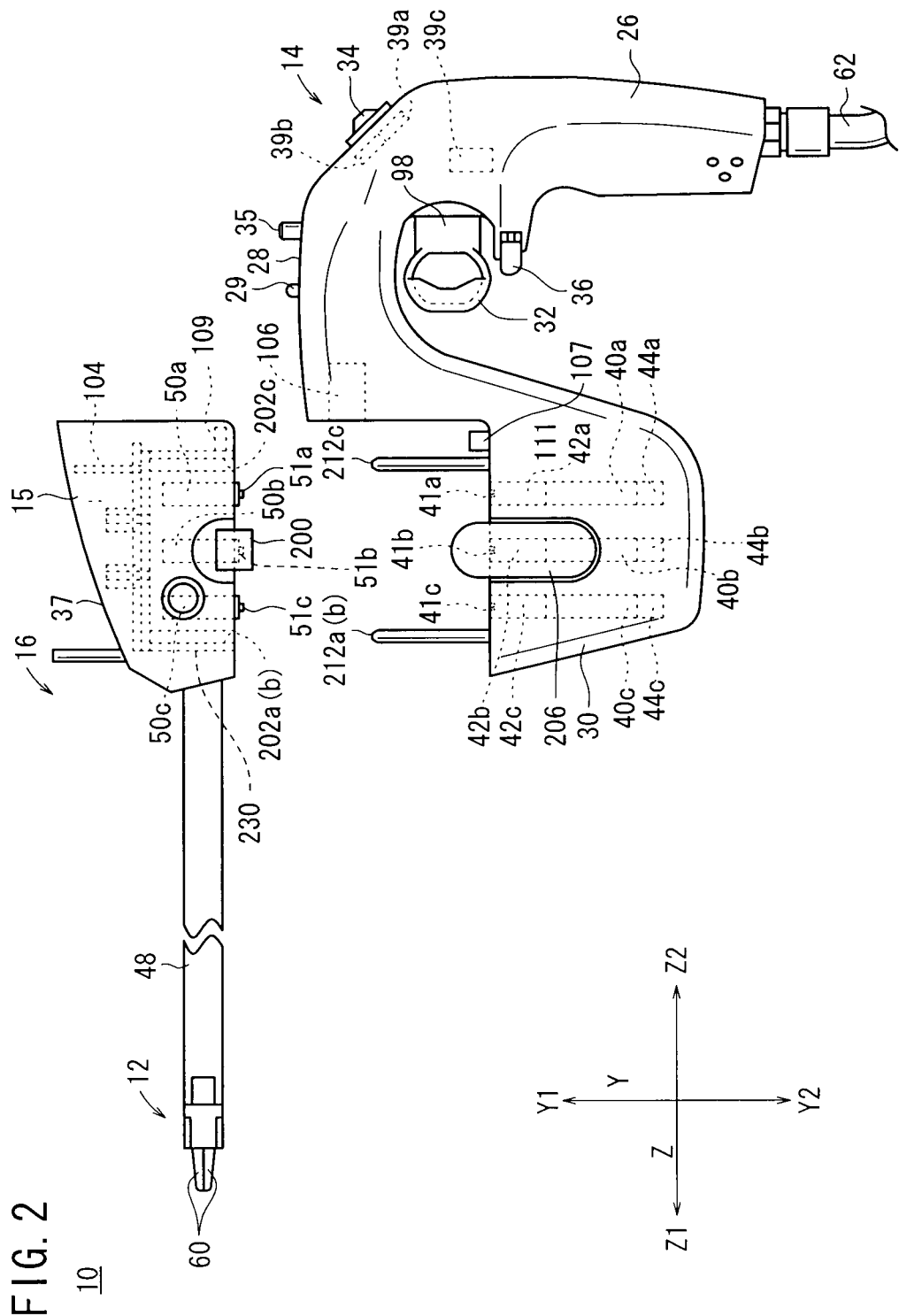
FIG. 2 is a side elevational view of the medical manipulator, with a working unit and an operating unit being separated from each other.
Figure 3:
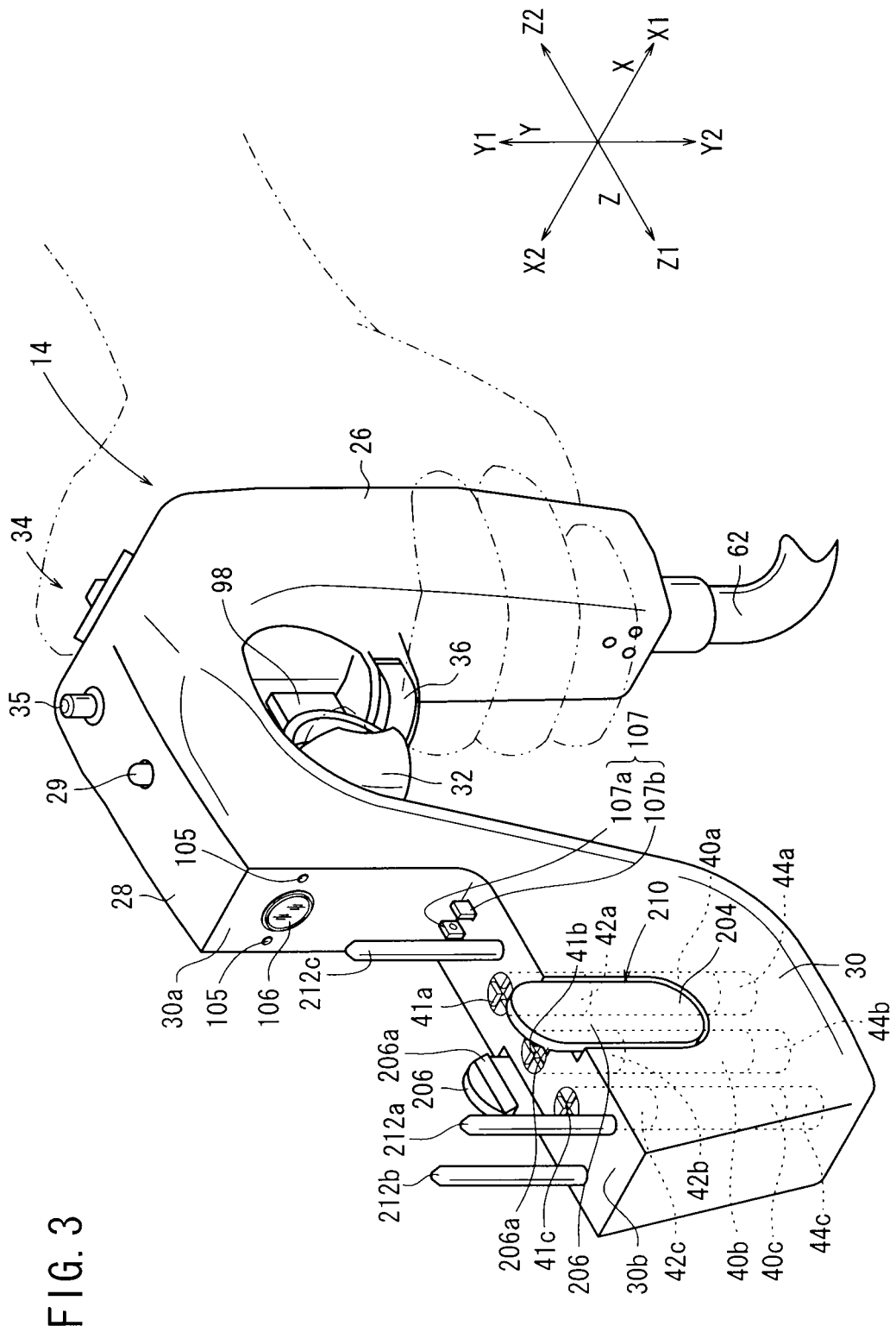
FIG. 3 is a perspective view of the operating unit.

As shown in FIGS. 1, 2 and 3, the manipulator 10 has a distal-end working unit (first distal-end working unit) 12 for gripping a portion of a living tissue, a curved needle or the like for performing a given surgical treatment. The curved needle usually is referred to as a needle driver or a needle holder.

The manipulator 10 comprises an operating unit 14 on a proximal end portion thereof, which is held and operated by a human hand, and a working unit 16 detachably mounted on the operating unit 14. The operating unit 14 is electrically detachably connected to a controller 27 by a connector 24, thereby making up a manipulator system.

The manipulator 10 basically includes the operating unit 14 and the working unit 16. The controller 27 for electrically controlling the manipulator 10 is connected by the connector 24 to a cable 62, which extends from the lower end of a grip handle 26 of the operating unit 14. Some or all of the functions of the controller 27 may be incorporated into the operating unit 14.

In the following descriptions, transverse directions in FIG. 1 shall be referred to as X directions, vertical directions as Y directions, and longitudinal directions of a hollow joint shaft 48 as Z directions. Among the X directions, the rightward direction as viewed from the distal end is referred to as an X1 direction, while the leftward direction is referred to as an X2 direction. Among the Y directions, the upward direction is referred to as an Y1 direction, while the downward direction is referred to as an Y2 direction. Among the Z directions, the forward direction is referred to as a Z1 direction, while the rearward direction is referred to as a Z2 direction. Unless otherwise noted, these directions represent directions of the manipulator 10 when the manipulator 10 is in a reference attitude (neutral attitude). The above directional definitions are for illustrative purposes only, and the manipulator 10 can be used in any of various orientations. For example, the manipulator 10 may be used upside down.

The working unit 16 comprises a distal-end working unit 12 for performing a working operation, a connector 15 connected to an actuator block (actuator) 30 of the operating unit 14, and an elongate hollow joint shaft 48 connecting the distal-end working unit 12 and the connector 15 to each other. When a predetermined action is performed on the actuator block 30, the working unit 16 can be separated from the operating unit 14, so that the working unit 16 can be cleaned, sterilized, and serviced for maintenance.

The distal-end working unit 12 and the joint shaft 48, which are small in diameter, can be inserted into a body cavity 22 through a trocar 20 in the form of a hollow cylinder mounted in an abdominal region or the like of a patient. The distal-end working unit 12 is actuated by the operating unit 14 in order to perform various surgical techniques, to remove, grip, suture, or ligate an affected part of the patient's body within the body cavity 22.

The operating unit 14 will be described in detail below.

The operating unit 14 includes a grip handle 26 gripped by a human hand, a bridge 28 extending from an upper portion of the grip handle 26, and an actuator block 30 connected to a distal end of the bridge 28.

The connector 15 has two engaging teeth 200 disposed respectively on opposite side surfaces thereof and three fitting holes 202a, 202b, 202b defined therein, which are open at a lower surface thereof. The three fitting holes 202a, 202b, 202c are disposed near ends of the connector 15 in the Z1 and Z2 directions, and extend in the Y direction.

The actuator block 30 houses therein three motors (DC motors) 40a, 40b, 40c, which extend parallel to each other, and are arrayed at spaced intervals along the Z direction. The motors 40a, 40b, 40c are energized under the control of the controller 27, based on actions made by the operator on the operating unit 14. The motors 40a, 40b, 40c are small in size and diameter, and the actuator block 30 that houses the motors 40a, 40b, 40c therein has a flat compact shape. The motors 40a, 40b, 40c are combined with respective speed reducers 42a, 42b, 42c, each in the form of a planetary gear assembly, for example, having a speed reduction ratio ranging from 1:100 to 1:300.

The actuator block 30 is disposed downwardly of the end of the operating unit 14 in the Z1 direction. The actuator block 30 implies a body on which the working unit 16 is mounted. The actuator block 30 is not limited to a structure for storing the motors 40a, 40b, 40c therein, but also covers a joint surface 30a (see FIG. 3) connected to the bridge 28.

The motors 40a, 40b, 40c also are combined with respective rotary encoders 44a, 44b, 44c for detecting angular displacements of their respective drive shafts. The rotary encoders 44a, 44b, 44c supply detected angle signals, respectively, to the controller 27.

As shown in FIGS. 2 and 3, the grip handle 26 extends in the Y2 direction from the end of the bridge 28, and has a length suitable for being gripped by a human hand. The grip handle 26 has an input means for entering signals for operating the distal-end working unit 12. The input means includes a trigger lever 32 and a switch 36 disposed in close proximity to the grip handle 26, which projects away from the grip handle 26 in the Z1 direction, and a composite input unit 34 and an operation switch 35 facing away from the grip handle 26 in the Y1 direction. The input unit 34 is operated by an operator's thumb.

An LED 29 is mounted on the upper surface of the bridge 28 at a location that can easily be viewed by the operator of the manipulator 10. The LED 29 is spaced from the operation switch 35 in the Z1 direction. The LED 29 serves as an indicator for indicating a controlled state of the manipulator 10. The LED 29 is of a size large enough to be easily visually recognizable by the operator, and yet is sufficiently small and lightweight, so as not to interfere with the operation of the manipulator 10.

The cable 62 connected to the controller 27 has an end connected to the lower end of the grip handle 26. The grip handle 26 and the cable 62 may be connected to each other by a connector.

The operation switch 35 serves to selectively enable or disable the manipulator 10. The LED 29 is located in a visually recognizable position substantially centrally on the upper surface of the bridge 28, in juxtaposed relation to the operation switch 35. The LED 29 is turned on in synchronism with the operation switch 35, when the operation switch 35 is turned on. Therefore, when the operator turns the operation switch 35 on or off, the operator can reliably recognize and confirm that the operation switch 35 has been turned on or off, by visually checking the LED 29.

The controller 27 reads the state of the operation switch 35. When the operation switch 35 is turned on, the controller 27 sets the manipulator 10 to an operation mode. When the operation switch 35 is turned off, the controller 27 sets the manipulator 10 to an automatic origin return mode, and returns the motors 40a, 40b, 40c to their origins. After the motors 40a, 40b, 40c have been returned to their origins, the controller 27 sets the manipulator 10 in a stop mode. While in the operation mode, the controller 27 enables operation commands to be entered from the operating unit 14 so as to energize the motors 40a, 40b, 40c. In the stop mode, the controller 27 stops the motors 40a, 40b, 40c, regardless of whether operation commands are entered from the operating unit 14 or not. The controller 27 distinguishes between these modes, and switches between different energized states of the LED 29 based on the distinguished modes.

More specifically, when the manipulator 10 is in the operation mode, the controller 27 energizes the LED 29 to emit green light. When the manipulator 10 is in the stop mode, the controller 27 de-energizes the LED 29. When the manipulator 10 is in the automatic origin return mode, upon switching from the operation mode to the stop mode, the controller 27 energizes the LED 29 to emit red light.

The composite input unit 34 serves as a composite input means, including a shuttle ring 100 (see FIG. 4) for supplying rotational commands in rolling directions (shaft rotating directions) to the distal-end working unit 12, and a pad 132 (see FIG. 4) for supplying yawing directions (left and right directions) to the distal-end working unit 12. The trigger lever 32 serves as an input means for supplying opening and closing commands to a gripper 60 (first opening and closing mechanism) 60 (see FIGS. 1 and 6) of the distal-end working unit 12.

The composite input unit 34 and the trigger lever 32 are combined with input sensors 39a, 39b, 39c (see FIG. 2), which serve to detect strokes upon movement thereof. The input sensors 39a, 39b, 39c supply detected stroke signals to the controller 27.

The trigger lever 32 is disposed slightly below the bridge 28 and projects in the Z1 direction. The trigger lever 32 is disposed in a position where it can easily be operated by the index finger of the hand that is gripping the grip handle 26.

The trigger lever 32 is operatively connected to the grip handle 26 by an arm 98, and is movable toward and away from the grip handle 26. The arm 98 is connected to the input sensor 39c inside the grip handle 26. The distance that the trigger lever 32 has moved toward or away from the grip handle 26 is detected by the input sensor 39c, which supplies a signal representative of the detected distance to the controller 27. The trigger lever 32 can be pulled toward the grip handle 26 in the Z2 direction by a finger that is held thereagainst, and can also be pushed away from the grip handle 26 in the Z1 direction by the finger. When the trigger lever 32 is thus pulled or pushed, the controller 27 receives a signal from the input sensor 39c, and supplies opening and closing commands to the gripper 60.

The switch 36, which is spaced from the trigger lever 32 in the Y2 direction, comprises an alternate switch. When the switch 36 is operated, the distal-end working unit 12 is returned to its origin, however, only in the rolling directions thereof.

A working unit detecting means 107, for detecting whether the connector 15 has been placed on the actuator block 30 or not, is disposed on an upper surface 30b of the actuator block 30 at an end thereof in the Z2 direction. The working unit detecting means 107 comprises an LED 107a serving as a light emitter and a photodiode 107b serving as a light detector, which are positioned in confronting relation to each other. When a light shield 109 (see FIG. 2) in the rear end of the connector 15 is inserted between the LED 107a and the photodiode 107b, the light shield 109 blocks light emitted from the LED 107a toward the photodiode 107b, thereby detecting that the connector 15 is mounted on the actuator block 30. The LED 107a and the photodiode 107b confront each other in the X direction and are disposed closely to each other.

The actuator block 30 includes a pair of independent engaging fingers 210 for holding the connector 15 of the working unit 16, and three alignment pins 212a, 212b, 212c for positioning and holding the connector 15.

The two engaging fingers 210 are pivotally mounted in symmetrical positions on respective outer side surfaces thereof, which face in the X1 and X2 directions. The engaging fingers 210 comprise respective pusher surfaces 204 and respective levers 206 extending in the Y1 direction from the pusher surfaces 204. The levers 206 project slightly from the upper surface of the actuator block 30 in the Y1 direction, and have respective wedges 206a on upper inner surfaces thereof for engagement with respective engaging teeth 200 provided on outer side surfaces of the connector 15 when the connector 15 is mounted on the actuator block 30. The engaging fingers 210 normally are biased by resilient members (not shown), which act to displace the levers 206 inwardly toward each other.

The alignment pins 212a, 212b, 212c are disposed in alignment with the respective fitting holes 202a, 202b, 202c. Among the three alignment pins 212a, 212b, 212c, two of the alignment pins 212a and 212b are disposed near the end of the upper surface of the actuator block 30 in the Z1 direction, whereas the other alignment pin 212c is disposed near the other end of the upper surface of the actuator block 30 in the Z2 direction. The alignment pins 212a, 212b, 212c extend in the Y1 direction. Alignment pins 212a and 212b, which are disposed near the end of the upper surface of the actuator block 30 in the Z1 direction, are spaced from each other in the X direction.

Because the actuator block 30 has three alignment pins 212a, 212b, 212c, the connector 15 is supported by the actuator block 30 at three positions corresponding to the alignment pins 212a, 212b, 212c, and is simply and reliably positioned with respect to the actuator block 30. Since the three alignment pins 212a, 212b, 212c are not positioned in a linear array, but are positioned in a triangular pattern, the alignment pins 212a, 212b, 212c can hold the connector 15 stably even when subjected to twisting forces applied in any directions.

At least two of the alignment pins 212a, 212b, 212c are effective to reliably position and hold the connector 15 stably on the actuator block 30. If two such alignment pins are spaced from each other in the Z direction, then the alignment pins are effective to hold the connector 15 more stably on the actuator block 30.

Figure 4:
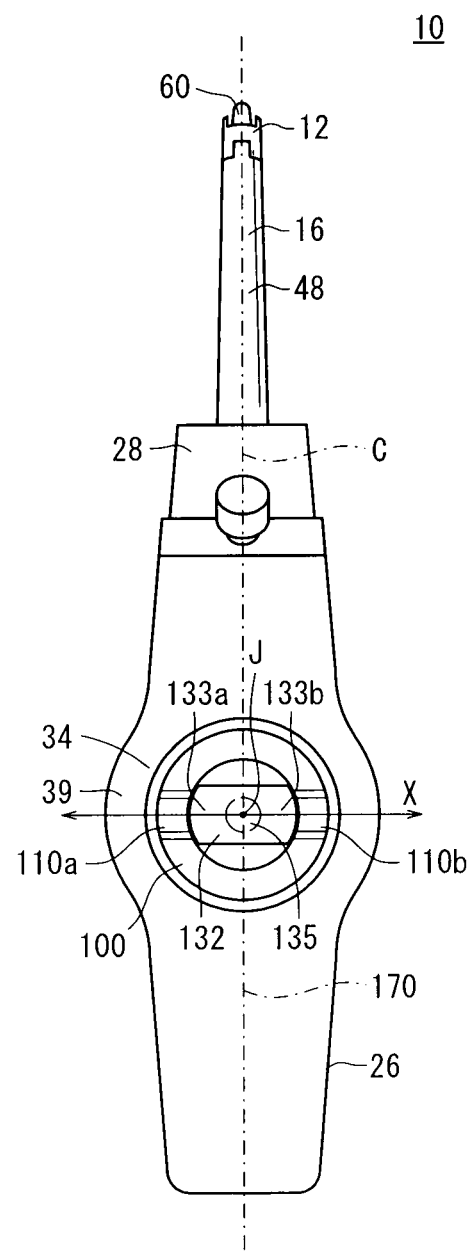
FIG. 4 is a plan view of the medical manipulator as seen along an axis of rotation of a shuttle ring.

As shown in FIG. 4, the shuttle ring 100 serves as an input means for applying rotational commands in rolling directions to the distal-end working unit 12. When the shuttle ring 100 is manually turned by a greater angular interval, the distal-end working unit 12 is angularly moved in a rolling direction at a greater angular speed. When the shuttle ring 100 is not manually turned, the distal-end working unit 12 is held at rest in the rolling directions. The shuttle ring 100 includes a pair of finger applying knobs 110a, 110b disposed in diametrically symmetric positions on the side face of the shuttle ring 100, which faces outwardly along the direction of an axis J thereof.

Inasmuch as the shuttle ring 100 has an annular shape, the shuttle ring 100 is easily visually recognized as an input means for entering rolling commands. The operator can easily learn and will not quickly forget how to use the shuttle ring 100.

As shown in FIG. 4, the shuttle ring 100 has a horizontally central line 170 aligned with the longitudinal axis C of the joint shaft 48, as viewed along the rotational axis J of the shuttle ring 100. Consequently, the operator can feel that the rolling mechanism of the distal-end working unit 12 operates concentrically with the shuttle ring 100, in a direct relationship therewith. Accordingly, the operator finds it easy to operate the manipulator 10.

The pad 132 is disposed within the shuttle ring 100. The pad 132 has left and right surfaces 133a, 133b on respective opposite sides of the rotational axis J. The pad 132 serves as an input means for imparting angular commands, for thereby tilting the distal-end working unit 12 when the left and right surfaces 133a, 133b of the pad 132 are pushed in. When the left and right surfaces 133a, 133b are pushed in at a greater depth, the distal-end working unit 12 is tilted at a greater rate. When the pad 132 is not operated, the distal-end working unit 12 is prevented from being tilted.

With the composite input unit 34 being thus constructed, the manipulator 10 can be used either by the right hand or the left hand, as it is horizontally symmetrical in shape. In FIG. 4, the manipulator 10 is illustrated in perspective for facilitating understanding of the way in which the manipulator 10 is seen from the viewpoint of the operator.

As shown in FIG. 4, the pad 132 and the shuttle ring 100 of the composite input unit 34 are coaxially disposed in a concentrated and compact configuration around the axis J.

For removing the connector 15 from the operating unit 14, the operator presses the pusher surfaces 204 of the engaging fingers 210 simultaneously toward each other, so as to tilt the levers 206 against the resiliency of the resilient members and bring the wedges 206a out of engagement with the engaging teeth 200. The connector 15 can now be pulled upwardly in the Y1 direction and removed from the operating unit 14. While the connector 15 is disposed on the actuator block 30, since the three alignment pins 212a, 212b, 212c on the upper surface 30b of the actuator block 30 are fitted respectively into the fitting holes 202a, 202b, 202c in the connector 15, the connector 15 is stably held on the actuator block 30.

In order to connect the connector 15 to the operating unit 14, the operator aligns the alignment pins 212a, 212b, 212c respectively with the fitting holes 202a, 202b, 202c, and inserts the alignment pins 212a, 212b, 212c respectively into the fitting holes 202a, 202b, 202c by lowering the connector 15 in the Y2 direction. The levers 206 of the engaging fingers 210 are displaced outwardly while sliding over the outer surfaces of the engaging teeth 200. The levers 206 snap back under the resiliency of the resilient members, thereby bringing the wedges 206a into engagement with the engaging teeth 200. In such a situation, the connector 15 is now completely mounted on the actuator block 30.

On the joint surface 30a of the operating unit 14, a camera 106 is mounted for reading a QR code of an ID card 104 (see FIG. 5) of the connected working unit 16, and supplying the read QR code to the controller 27. Two LEDs 105, for illuminating the ID card 104 of the connected working unit 16, also are mounted on the joint surface 30a of the operating unit 14. The camera 106 is disposed in a position facing the ID card 104, and the two LEDs 105 are positioned one on each side of the camera 106. The camera 106 may be replaced with a bar-code reader or a bar-code scanner, for similarly reading an ID code of the ID card 104.

The working unit 16 will be described in detail below. After a surgical operation using the manipulator 10 has been completed, the working unit 16 can be removed from the operating unit 14 and cleaned. The working unit 16 may also periodically be replaced with a new one for achieving sufficient reliability. Since the working unit 16 does not include any electronic devices therein, the working unit 16 is inexpensive. In addition, in view of the mechanical service life of the working unit 16, which is affected by the distal-end working unit 12 as the distal-end working unit 12 experiences burdens due to operations within the body cavity 22, and also in view of damage caused when the working unit 16 is cleaned with steam and heat, the working unit 16 may be replaced with a new working unit 16 at appropriate times. In view of the general service life of the working unit 16, the manufacturer of the working unit 16 sets a limit number of times, up to which the working unit 16 can repeatedly be used. A managerial person, who works for the medical organization that uses the manipulator 10, counts the number of times that the working unit 16 has been used, and discards the working unit 16 according to a given procedure when the limit on the number of times has been reached or exceeded.

Figure 5:
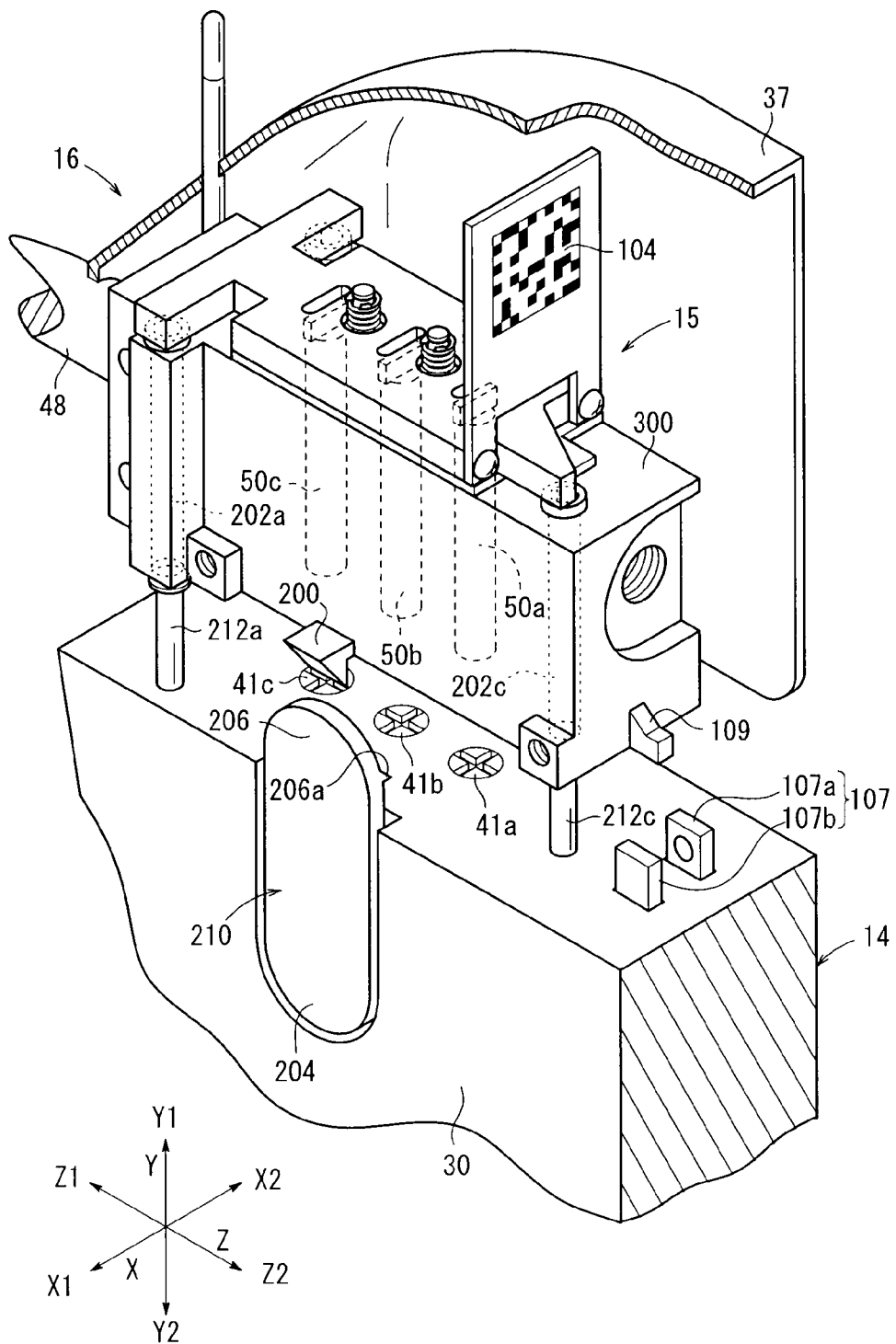
FIG. 5 is a perspective view, partially cut away, of a connector of the medical manipulator.

As shown in FIGS. 1, 2, and 5, a resin cover 37 covers the connector 15 of the working unit 16. The connector 15 houses and supports pulleys 50a, 50b, 50c rotatably therein, which are connected to the respective drive shafts of the motors 40a, 40b, 40c and are rotated by the motors 40a, 40b, 40c.

Wires 54a, 54b, 54c (see FIGS. 6 and 8) are trained respectively around the pulleys 50a, 50b, 50c and extend through a space in the joint shaft 48 toward the distal-end working unit 12. The wires 54a, 54b, 54c have portions fixed to the pulleys 50a, 50b, 50c (as well as to the pulleys 57a, 57b, 57c to be described later) so that the wires 54a, 54b, 54c will not slip on the pulleys 50a, 50b, 50c. The wires 54a, 54b, 54c may all be of the same type and have the same diameter.

The pulleys 50a, 50b, 50c in the connector 15 have respective criss-cross coupling teeth 51a, 51b, 51c on lower ends thereof in the Y2 direction, whereas the rotatable shafts of the motors 40a, 40b, 40c in the actuator block 30 have respective criss-cross coupling recesses 41a, 41b, 41c. The coupling teeth 51a, 51b, 51c are engageable in the respective coupling recesses 41a, 41b, 41c. When the connector 15 is mounted on the actuator block 30, the coupling teeth 51a, 51b, 51c engage within the respective coupling recesses 41a, 41b, 41c, for enabling the rotation of the motors 40a, 40b, 40c to be transmitted to the pulleys 50a, 50b, 50c. The coupling teeth 51a, 51b, 51c and the coupling recesses 41a, 41b, 41c may also have different shapes other than criss-cross shapes.

As shown in FIG. 5, the ID card 104, which carries an ID (identification) mark for identifying an individual working unit 16, is disposed on the connector 15 near the rear end thereof.

The ID mark carried by the ID card 104 comprises a QR code in the form of a two-dimensional bar code for identifying the working unit 16. The QR code is peculiar to a single working unit 16, and hence different QR codes are assigned to each of the different working units 16, respectively. The QR code contains various pieces of information, including the type, specifications, serial number, production factory, production date, tradename, etc., of the working unit 16.

Figure 6:
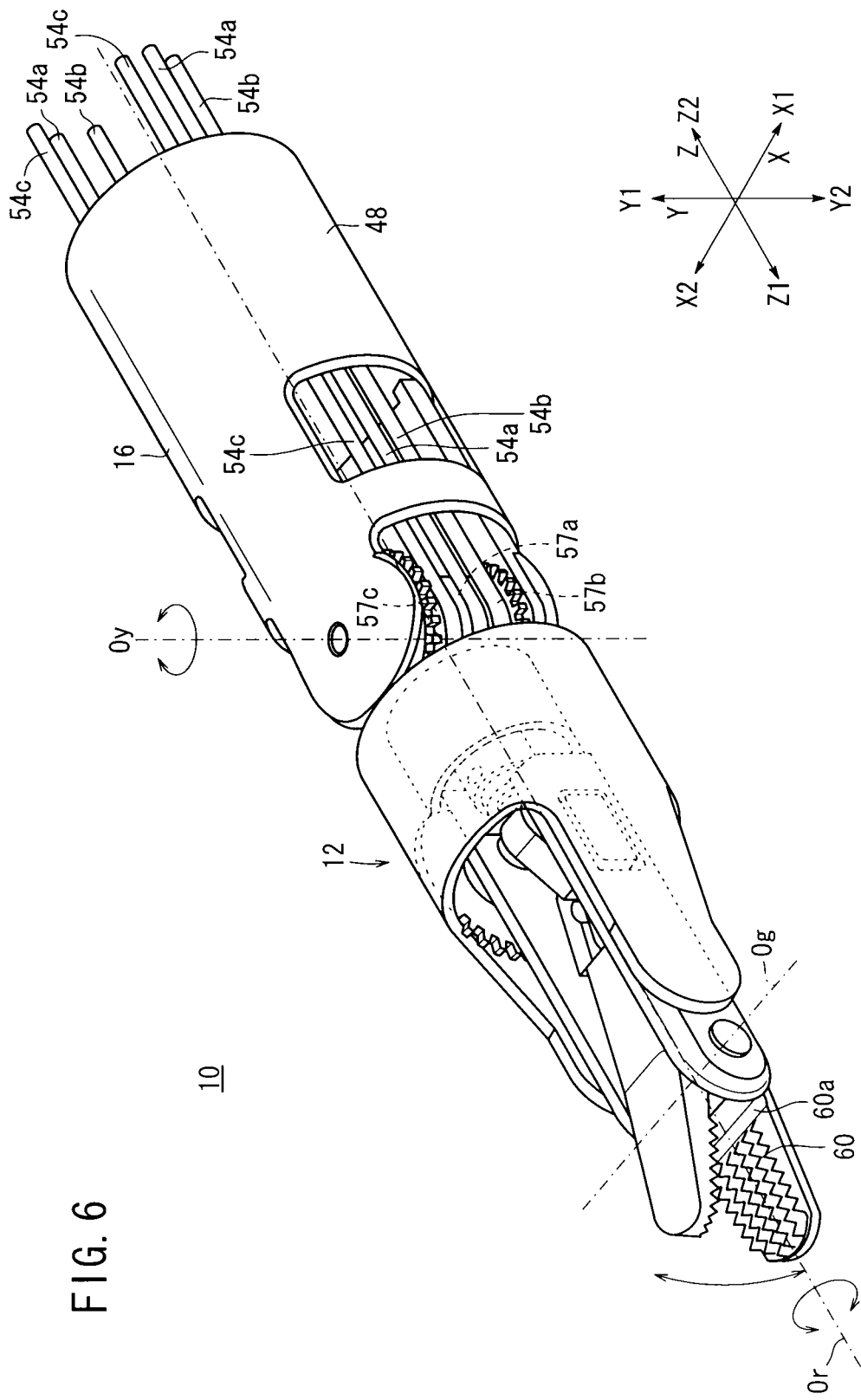
FIG. 6 is a perspective view of a distal-end working unit of the medical manipulator.

As shown in FIG. 6, the wires 54a, 54b, 54c, which extend through the joint shaft 48, are trained respectively around the pulleys (distal end rotors) 57a, 57b, 57c that are disposed in the distal-end working unit 12, which includes the gripper 60.

When the pulley 50a is rotated about its own axis by the motor 40a, rotation of the pulley 50a is transmitted through the wire 54a to the pulley 57a, thereby rotating the pulley 57a about its axis. Rotation of the pulley 57a is then transmitted to gears, which selectively open and close the gripper 60. At least one of a pair of opening and closing members making up the gripper 60 has a shallow and narrow groove 60a extending in a direction X at proximal end thereof. The groove 60a is smoothly formed.

Figure 7:
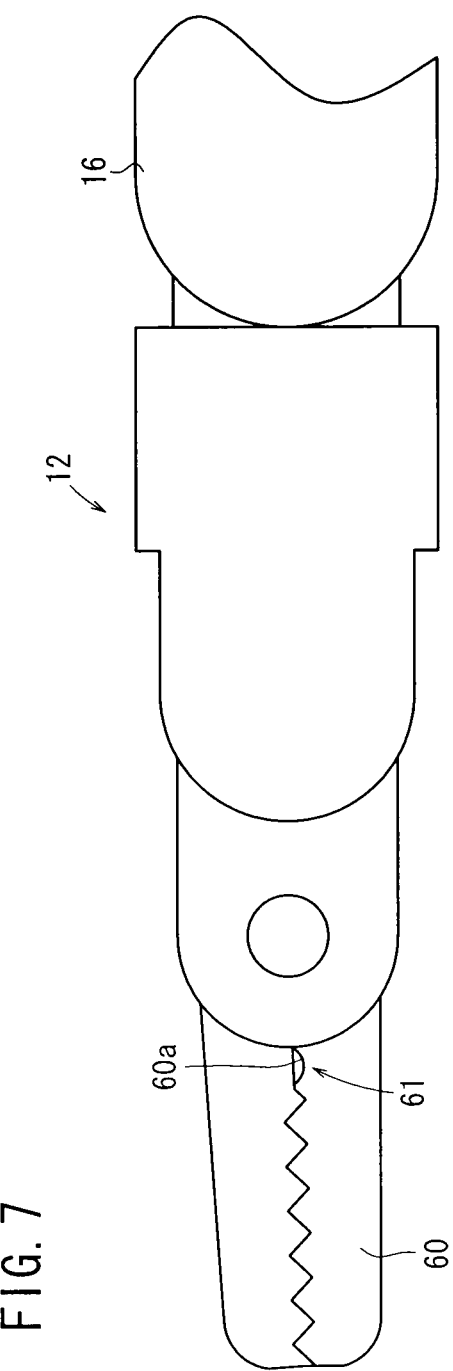
FIG. 7 is a side view of a distal-end working unit of the medical manipulator.

As shown in FIG. 7, when the gripper 60 is closed, the groove 60a forms a hole 61. The hole 61 is narrow and has a size just enough to insert a suture strand 314 to be described later. As long as the hole 61 can be formed, the 60a does not necessarily extend in the X direction.

Figure 8:
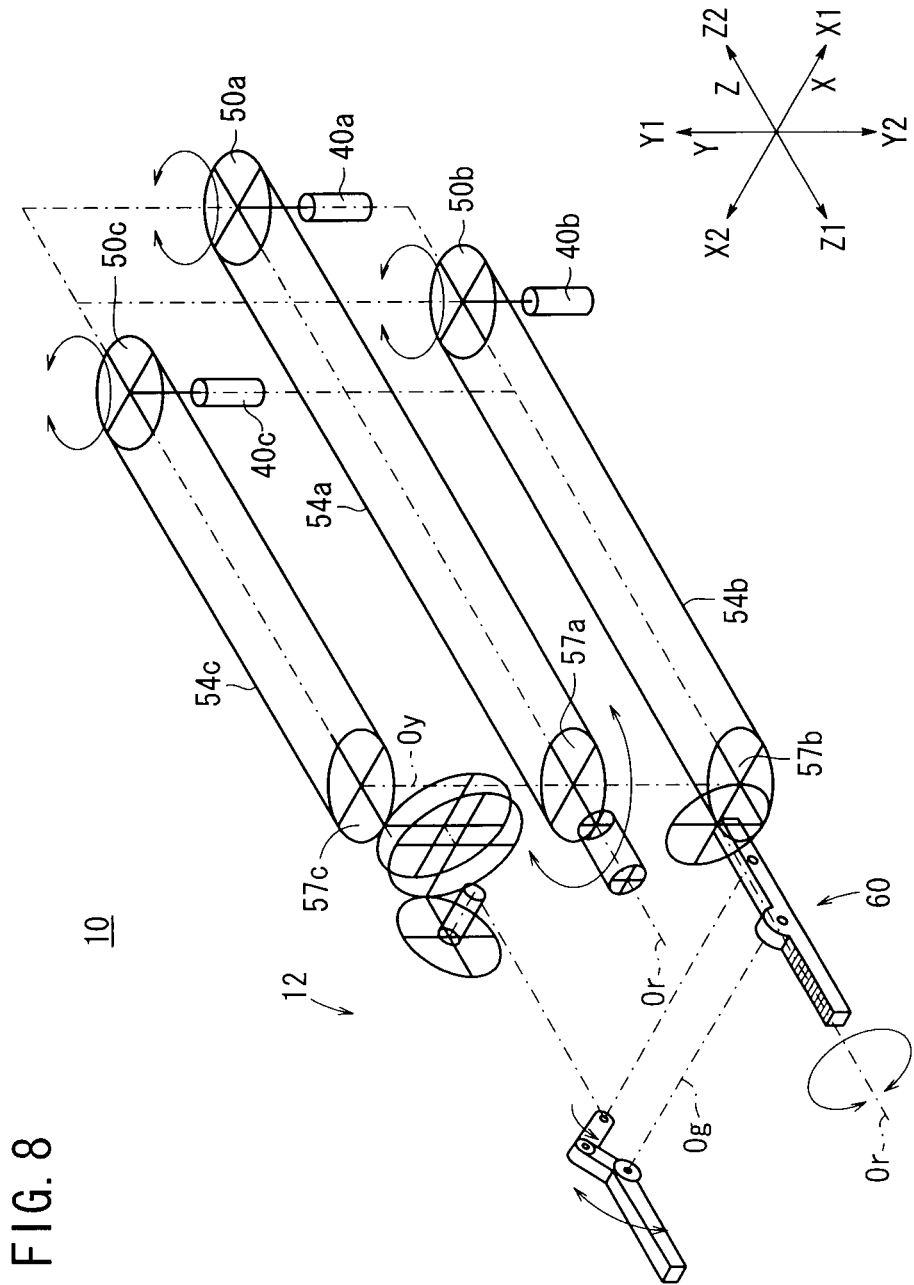
FIG. 8 is a schematic perspective view of a basic assembly of pulleys, wires, and the distal-end working unit of the medical manipulator.

As shown in FIG. 8, the pulleys 50a, 50b, 50c, the wires 54a, 54b, 54c, and the pulleys 57a, 57b, 57c jointly make up a power transmitting assembly, which operates mechanisms having three degrees of freedom incorporated within the distal-end working unit 12, for twisting the distal-end working unit 12 in rolling directions about an axis Or, turning the distal-end working unit 12 horizontally about an axis Oy, and opening and closing the gripper 60 about an axis Og. Since each of the mechanisms having three degrees of freedom tend to interfere with each other, the motors 40a, 40b, 40c are energized to operate the mechanisms, while preventing interference between each of the mechanisms.

The motors 40a, 40b, 40c are energized under the control of the controller 27 based on signals generated by the input sensors 39a, 39b, 39c, which detect movement strokes of the composite input unit 34 and the trigger lever 32.

When the wires 54a, 54b, 54c are assembled together with the pulleys 50a, 50b, 50c and the pulleys 57a, 57b, 57c, the wires 54a, 54b, 54c are adjusted in advance so as to be kept under a suitable degree of tension between the pulleys 50a, 50b, 50c and the pulleys 57a, 57b, 57c. Each of the wires 54a, 54b, 54c is in the form of a loop inside the joint shaft 48, and comprises two parallel runs inside the joint shaft 48.

In FIG. 8, the mechanism for twisting the distal-end working unit 12 in rolling directions about the axis Or is referred to as a rolling mechanism, the mechanism for opening and closing the gripper 60 about the axis Og is referred to as an opening and closing mechanism, and the mechanism for turning the distal-end working unit 12 horizontally about the axis Oy is referred to as a tilting mechanism.

Figure 9:
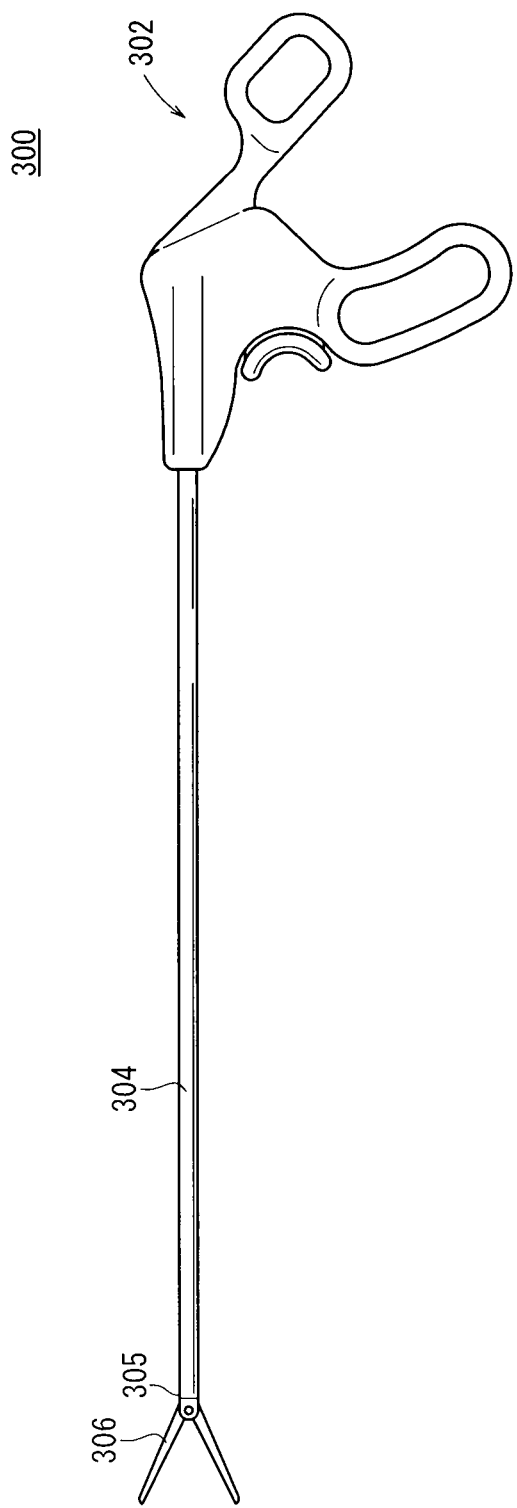
FIG. 9 is a side elevational view of a forceps.

FIG. 9 shows a forceps 300, which functions as a second manipulator for use in the intracoelomic suturing and ligating methods, according to a preferred embodiment of the present invention. As shown in FIG. 9, the forceps 300 comprises a hand operating unit 302, a slender shaft 304 extending from the hand operating unit 302, and a distal-end working unit (second distal-end working unit) 305 including a gripper (second opening and closing mechanism) 306. The hand operating unit 302 comprises a pair of handles that are openable and closable by fingers inserted through the handles. The handles of the hand operating unit 302 are operatively coupled to the gripper 306 by a mechanism that extends through the shaft 304, such that when the handles are selectively opened and closed, the gripper 306 also is selectively opened and closed. The gripper 306 may be locked in a closed state by a lock means, not shown. The forceps 300 may be of a conventional nature. Alternatively, a manipulator, which is similar or identical to the manipulator 10 described above, may be used in place of the forceps 300.

An intracoelomic suturing and ligating method according to a first embodiment of the present invention, which is carried out using the manipulator 10 and the forceps 300, shall be described below with reference to FIG. 10.

The intracoelomic suturing and ligating method according to the first embodiment is performed after a certain preparatory process and a given surgical technique have been carried out, by inserting the manipulator 10 and the forceps 300 through respective trocars 20 into a body cavity during an endoscopic surgical operation. The operator, typically a surgeon, performs the intracoelomic suturing and ligating method while watching images captured by an endoscope, not shown.

Figure 11:
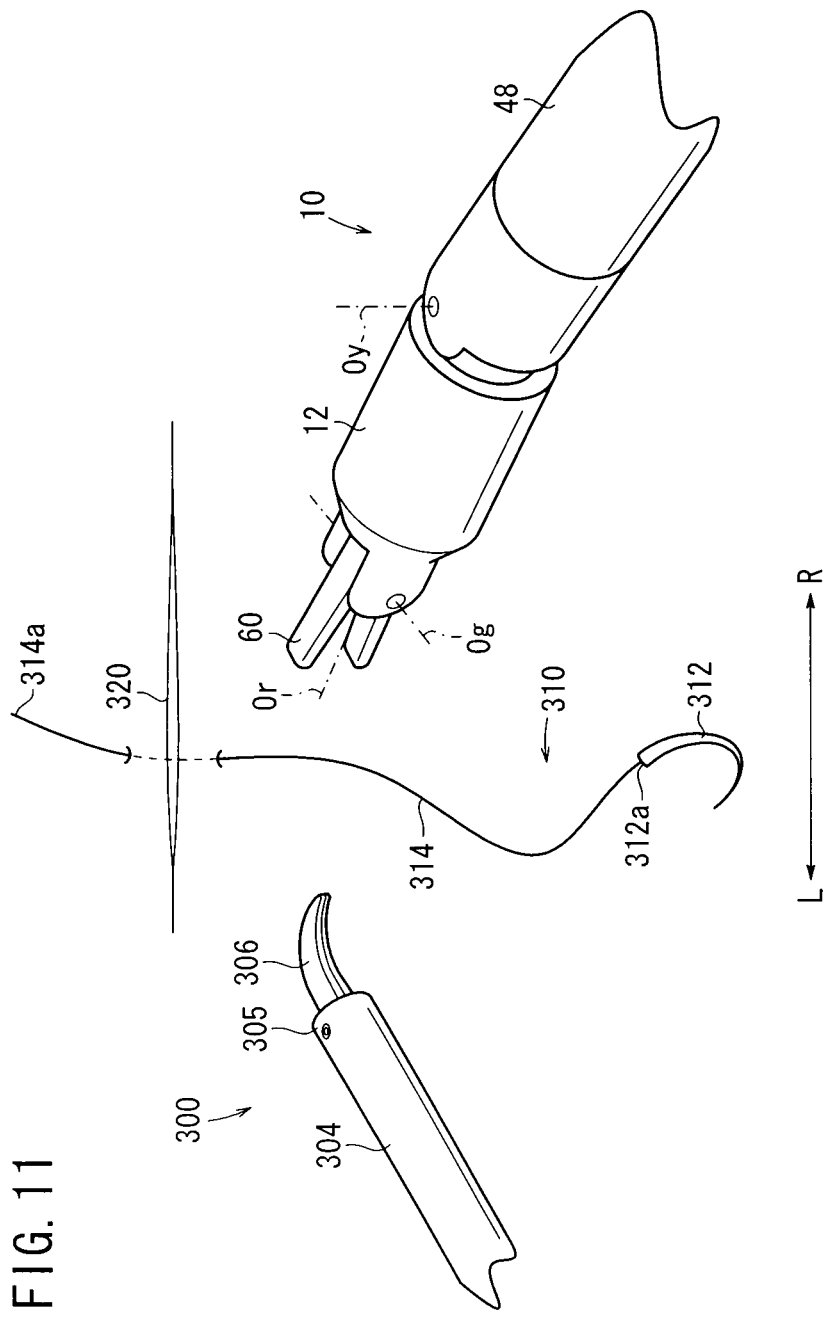
FIG. 11 is a fragmentary perspective view showing a needle piercing step of the intracoelomic suturing and ligating method according to the first embodiment.

In the following description, it is assumed that the manipulator 10, which is operated by the right hand of the operator, is positioned on the right side in FIG. 11, whereas the forceps 300, which is operated by the left hand of the operator, is positioned on the left side in FIG. 11. It is preferable for the manipulator 10 to be positioned on the side of the dominant hand of the operator.

Figure 12:
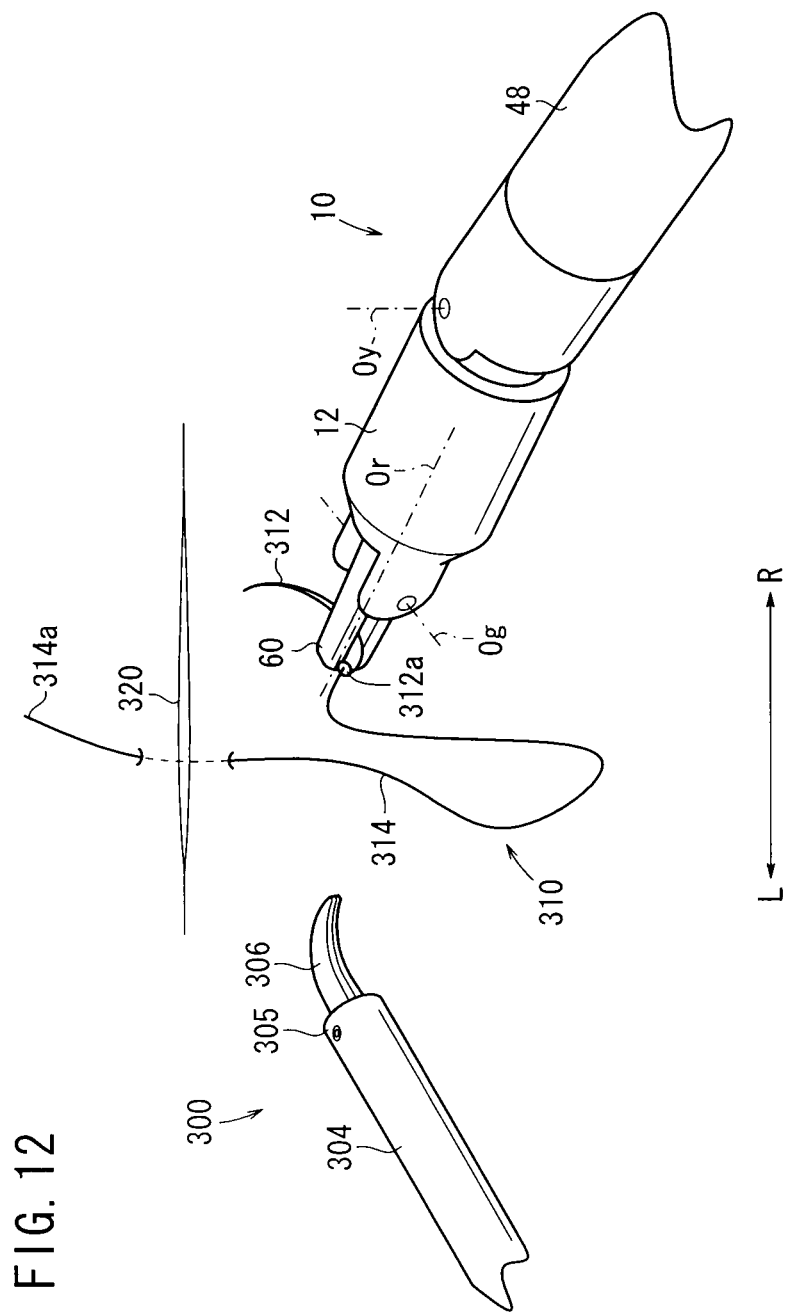
FIG. 12 is a fragmentary perspective view showing a needle gripping step of the intracoelomic suturing and ligating method according to the first embodiment.

It also is assumed that positions of the distal-end working unit 12 and the gripper 306 are defined by respective juxtaposed lateral directions, with the distal-end working unit 12 being in a right (R) direction and the gripper 306 being in a left (L) direction. As shown in FIG. 12, an upward (U) direction extends perpendicularly with respect to the lateral directions and directions normal to the sheet of FIG. 13. Further, a downward (D) direction also extends perpendicularly with respect to the lateral directions and directions normal to the sheet of FIG. 13. In some of FIGS. 11 through 41, which show surgical procedures carried out inside the body cavity, a suture strand 314 is shown as being interrupted where the suture strand 314 lies behind itself, for enabling easier understanding of the overlapping lengths of the suture strand 314.

Figure 10:
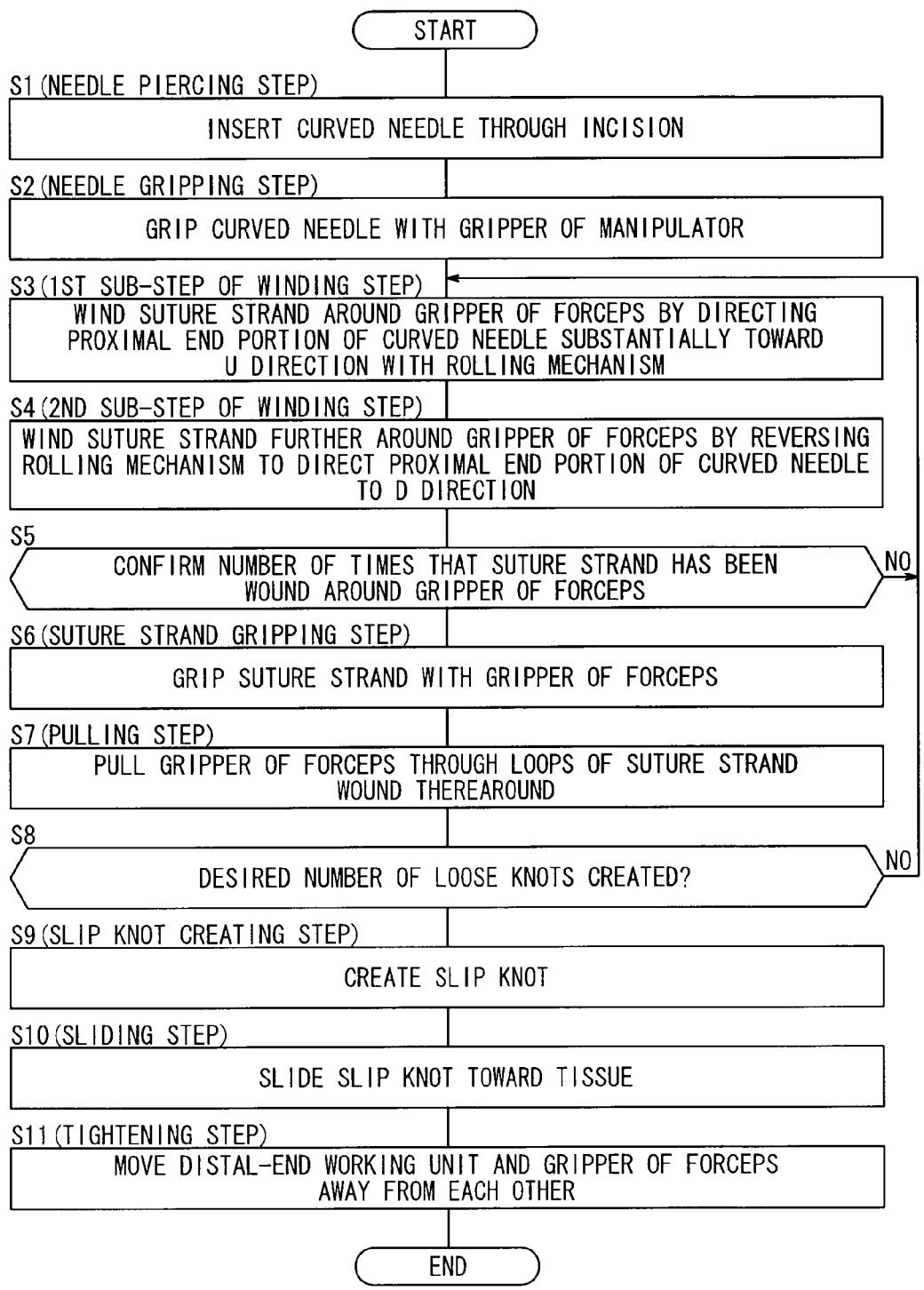
FIG. 10 is a flowchart of a sequence of an intracoelomic suturing and ligating method according to a first embodiment of the present invention.

In step S1 (needle piercing step) shown in FIG. 10, the curved needle 312 of a suture-needle assembly 310 is inserted through an incision (tissue) 320 in the body cavity as shown in FIG. 10. The suture strand 314 of the suture-needle assembly 310 includes an end portion 314a that is remote from the curved needle 312. The end portion 314a is not inserted through the incision (tissue) 320. The surgical procedure in step S1 is carried out using the manipulator 10, the forceps 300, or other means, or by using the manipulator 10, the forceps 300, and the other means in coordination with each other. The surgical procedure in step S1 is of a known nature and will not be described and illustrated in detail below.

The end portion 314a may be short, whereas the length of the suture strand 314 that is inserted through the incision 320 may be comparatively long, in order to make the subsequent surgical procedures easier to perform. According to the present embodiment, however, the length of the suture strand 314 that is inserted through the incision 320 should not be excessively long.

The suture-needle assembly 310 may utilize a straight needle rather than the curved needle 312. However, use of the curved needle 312 makes it easier for the operator to perform the surgical procedure in step S1.

In step S2 (needle gripping step), as shown in FIG. 12, the gripper 60 grips the curved needle 312. Subsequently, the gripper 60 continues to grip the curved needle 312 until one suturing cycle has been completed. For keeping the curved needle 312 in a gripped state, the gripper 60 may be locked in a closed state by a lock means. At this time, the suture strand 314 is positioned in front of the gripper 306, i.e., more closely to the operator.

In preparation for the following steps S3 and S4 (winding step), the distal-end working unit 12 is tilted slightly by the tilting mechanism from the longitudinal axis C of the joint shaft 48 toward the gripper 306, i.e., in the L direction. The distal-end working unit 12 and the gripper 60 are thus positioned closely to each other, for facilitating subsequent surgical procedures.

The gripper 306 remains closed prior to steps S3 and S4, in which the suture strand 314 is wound around the gripper 306. Since the gripper 306 is closed, the suture strand 314 is less liable to become entangled within the gripper 306, and the suture strand 314 can easily be coiled around the distal-end working unit 305.

Figure 13:
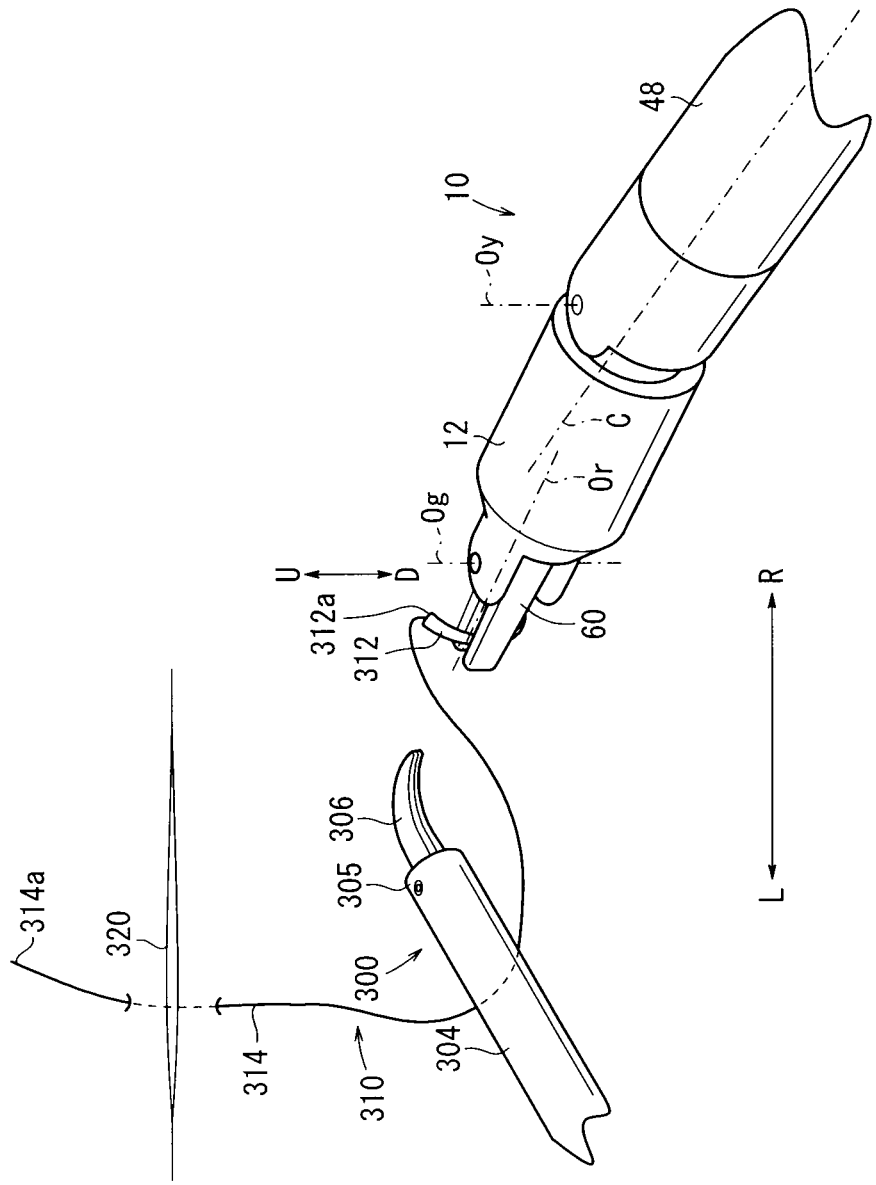
FIG. 13 is a fragmentary perspective view showing a first sub-step of a winding step of the intracoelomic suturing and ligating method according to the first embodiment.

In step S3 (first sub-step of the winding step), as shown in FIG. 13, a proximal end portion 312a of the curved needle 312, which is connected to the suture strand 314, is rolled substantially in the U direction by the rolling mechanism, thereby winding the suture strand 314 around the distal-end working unit 305 by about one-half turn.

At this time, the distal-end working unit 12 is turned in a direction to orient the proximal end portion 312a from the L direction (i.e., the distal-end working unit 12 is turned clockwise as viewed from the operator) in FIG. 13. The distal-end working unit 305 may be moved appropriately in view of the movement of the curved needle 312 and the position of the suture strand 314.

In step S3, the distal-end working unit 12 may be rolled while the distal-end working unit 12 itself is moved slightly toward the operator forwardly of the distal-end working unit 305, or while the distal-end working unit 305 is moved slightly away from the operator rearwardly of the distal-end working unit 12, so that the suture strand 314 lies beneath the distal-end working unit 305.

Figure 14:
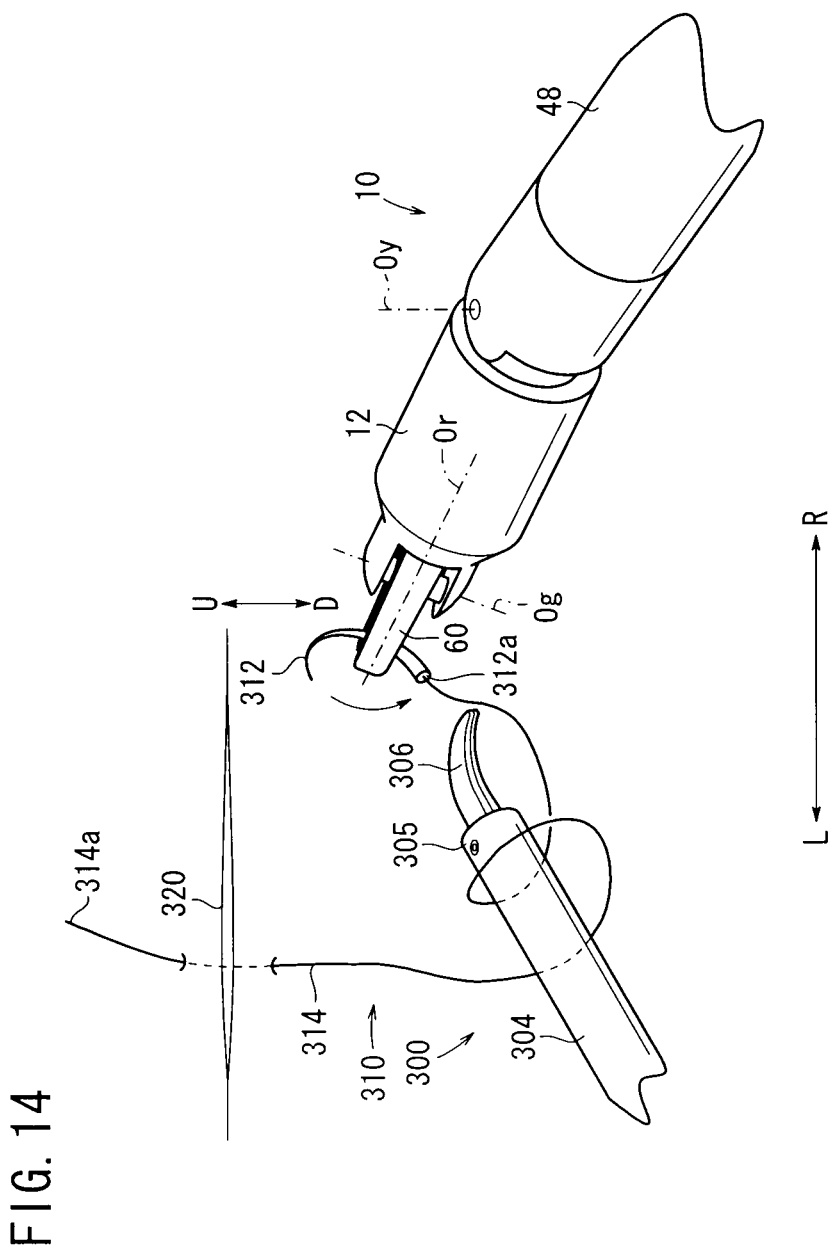
FIG. 14 is a fragmentary perspective view showing a second sub-step of the winding step of the intracoelomic suturing and ligating method according to the first embodiment.

In step S4 (second sub-step of the winding step), as shown in FIG. 14, the rolling mechanism is reversed so as to turn the proximal end portion 312a from the U direction toward the D direction and thereby wind the suture strand 314 further around an upper portion of the distal-end working unit 305 by about one-half turn. The suture strand 314 now is wound around the distal-end working unit 305 by a full turn.

At this time, the distal-end working unit 12 has been turned to orient the proximal end portion 312a via a position facing in the L direction toward the D direction (i.e., the distal-end working unit 12 is turned counterclockwise as viewed from the operator) in FIG. 13. The distal-end working unit 305 may be moved appropriately in view of the movement of the curved needle 312 and the position of the suture strand 314.

In step S4, the distal-end working unit 12 may be rolled while the distal-end working unit 12 itself is moved slightly away from the operator upwardly and rearwardly of the distal-end working unit 305, or while the distal-end working unit 305 is moved slightly toward the operator downwardly and forwardly of the distal-end working unit 12, so that the suture strand 314 lies above the distal-end working unit 305.

In steps S3 and S4, the above movements of the distal-end working unit 12 can be achieved by moving the operator's finger back and forth on the knob 110a or the knob 110b (see FIG. 4) of the shuttle ring 100. The shuttle ring 100, which serves as the rotary input means for controlling the rolling mechanism of the distal-end working unit 12, allows the operator to operate the manipulator 10 intuitively through a simple process.

When step S3 and step S4 are performed, the distal-end working unit 305 may be moved back and forth with respect to the other distal-end working unit 12, or alternatively, the proximal end portion 312a of the curved needle 312 may be vertically displaced relatively to the gripper 306, for easily winding the suture strand 314 around the distal-end working unit 305. For sufficiently displacing the proximal end portion 312a, the difference between the angular displacement of the rolling mechanism at the time of step S3 and the angular displacement of the rolling mechanism at the time of step S4 preferably should be about 180°. Actually, however, the difference between the angular displacements may be varied within a range from about 90° to 200° in order to sufficiently displace the proximal end portion 312a.

In step S5, the operator confirms the number of times that the suture strand 314 has been wound around the distal-end working unit 305. If the suture strand 314 has been wound around the distal-end working unit 305 a predetermined number of times (once or more, e.g., twice), then the intracoelomic suturing and ligating method proceeds to step S6. If the suture strand 314 has not been wound around the distal-end working unit 305 the predetermined number of times, then the intracoelomic suturing and ligating method returns to step S4.

Figure 15:
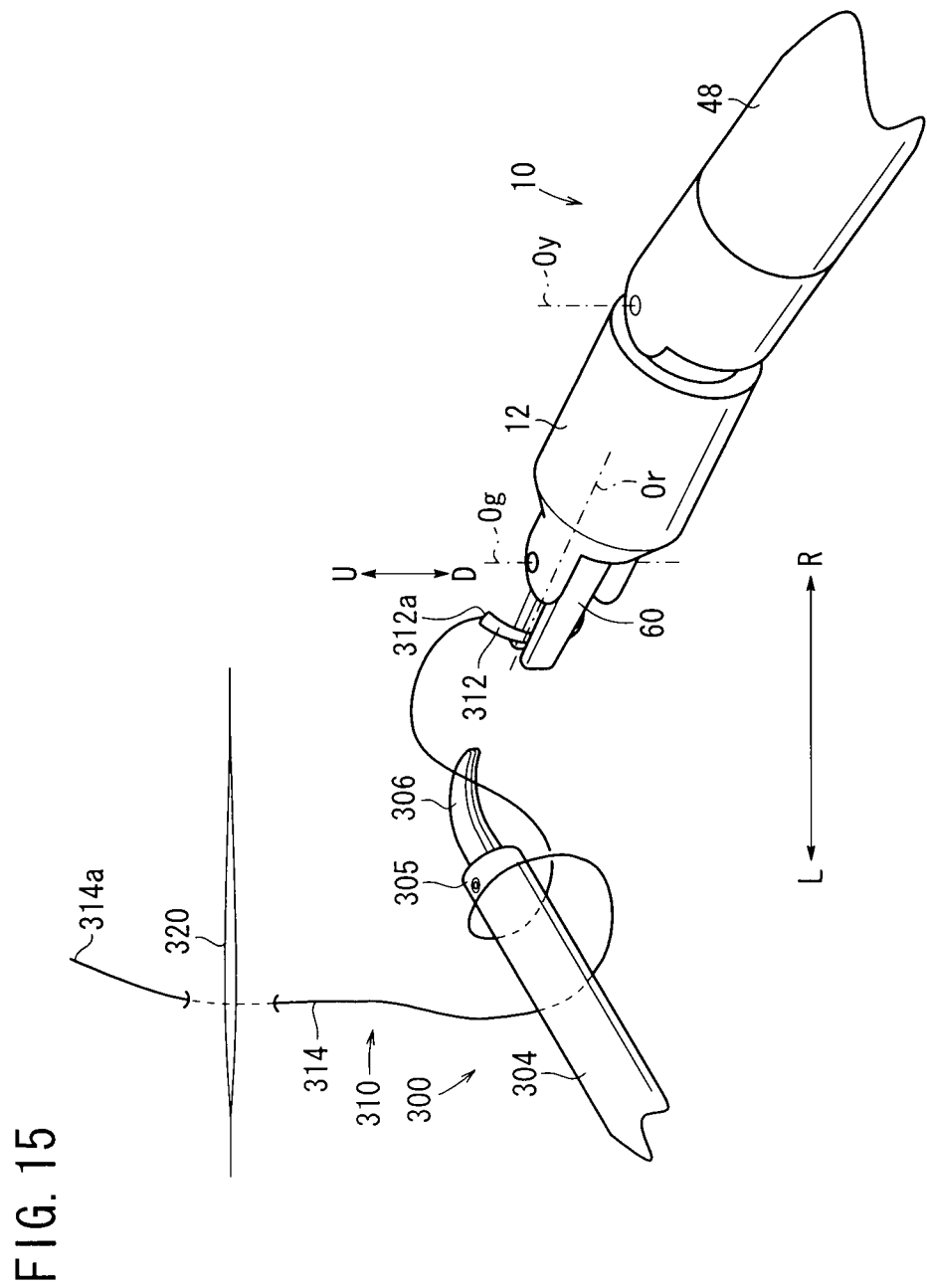
FIG. 15 is a fragmentary perspective view showing the first sub-step, performed for a second time, of the winding step of the intracoelomic suturing and ligating method according to the first embodiment.
Figure 16:
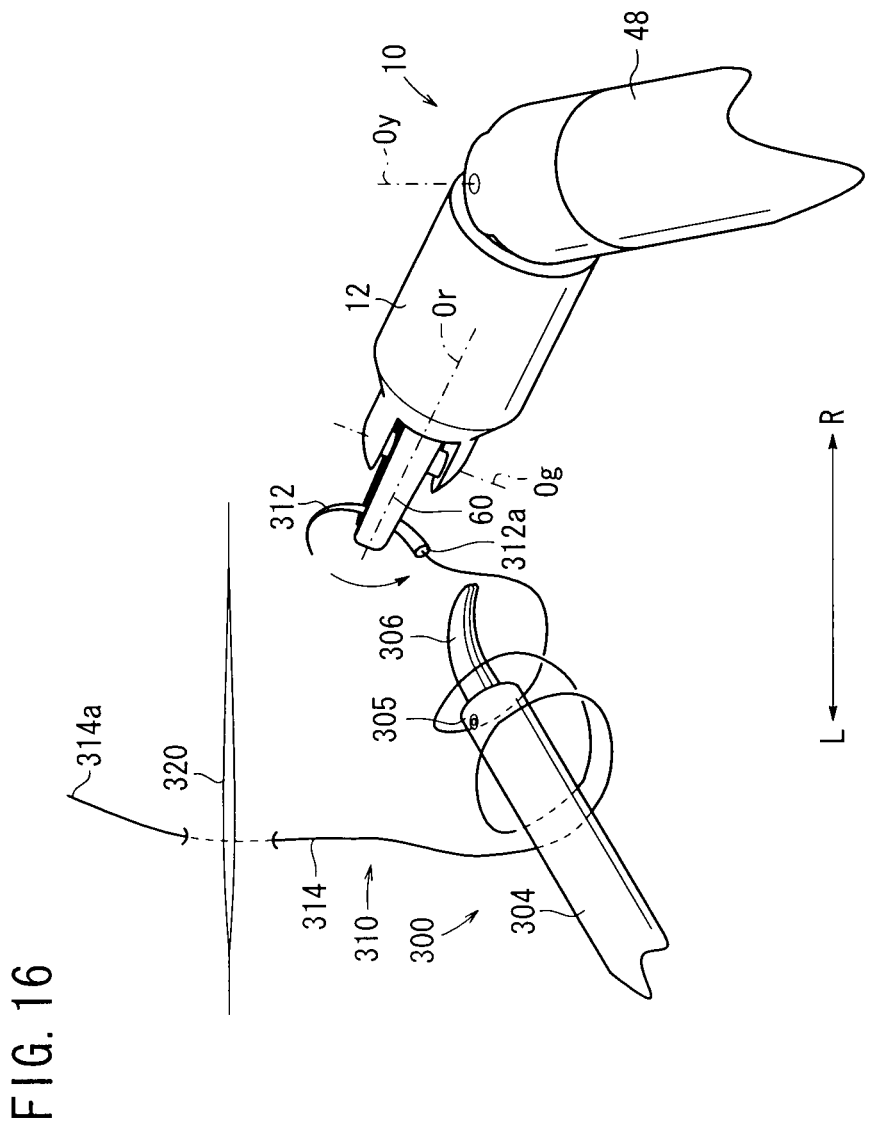
FIG. 16 is a fragmentary perspective view showing the second sub-step, performed for a second time, of the winding step of the intracoelomic suturing and ligating method according to the first embodiment.

For easier understanding of steps S3 and S4, the manner in which the suture strand 314 is wound around the distal-end working unit 305 twice is illustrated in FIGS. 15 and 16. The rolling mechanism is reversed (step S3) from the state shown in FIG. 15 so as to return the proximal end portion 312a to the U direction, thus winding the suture strand 314 around the distal-end working unit 305 twice, as shown in FIG. 15. Then, as shown in FIG. 16, the proximal end portion 312a is returned to the D direction, thereby winding the suture strand 314 around the distal-end working unit 305 twice. Thereafter, the intracoelomic suturing and ligating method proceeds to step S6. Steps S3 and S4 may be carried out at least once depending on surgical techniques and the operator's decision. Further, the number of times that the suture strand 314 is wound around the distal-end working unit 305 is at least once, and need not be an integral number of times. For example, the suture strand 314 is wound around the distal-end working unit 305 twice to form a double half knot, and once to form a single half knot.

Figure 17:
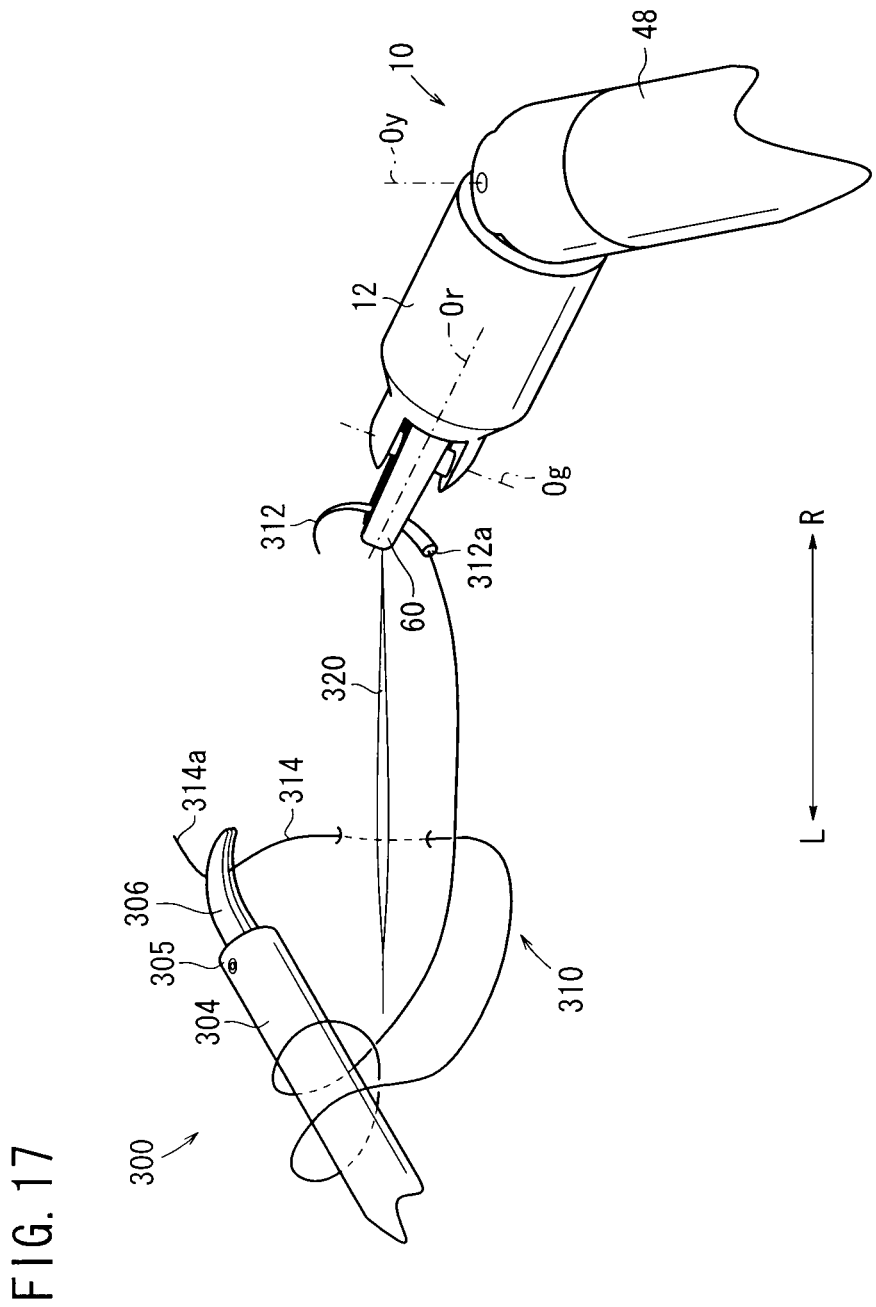
FIG. 17 is a fragmentary perspective view showing a suture strand gripping step of the intracoelomic suturing and ligating method according to the first embodiment.

In step S6 (suture strand gripping step), the gripper 306 is opened. Then, as shown in FIG. 17, the gripper 306 is closed again to grip a portion (e.g., the end portion 314a) of the suture strand 314, which is not inserted into the tissue.

Figure 18:
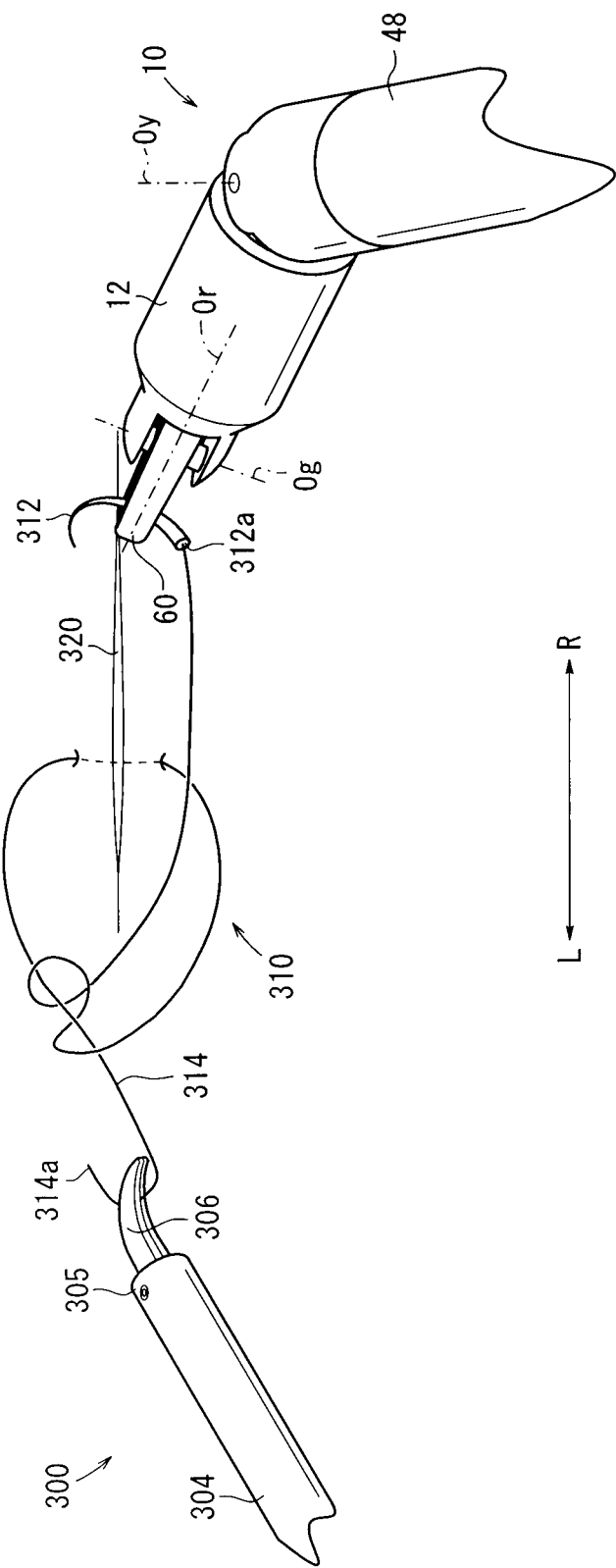
FIG. 18 is a fragmentary perspective view showing a pulling step of the intracoelomic suturing and ligating method according to the first embodiment.

In step S7 (pulling step), as shown in FIG. 18, the distal-end working unit 305 is pulled toward the operator, while the manipulator 10 is pushed away from the operator, thereby withdrawing the distal-end working unit 305 through the loops of the suture strand 314, which have been wound around the distal-end working unit 305. Depending on conditions inside the body cavity, either the distal-end working unit 305 may be pulled toward the operator, or the manipulator 10 may be pushed away from the operator.

Figure 19:
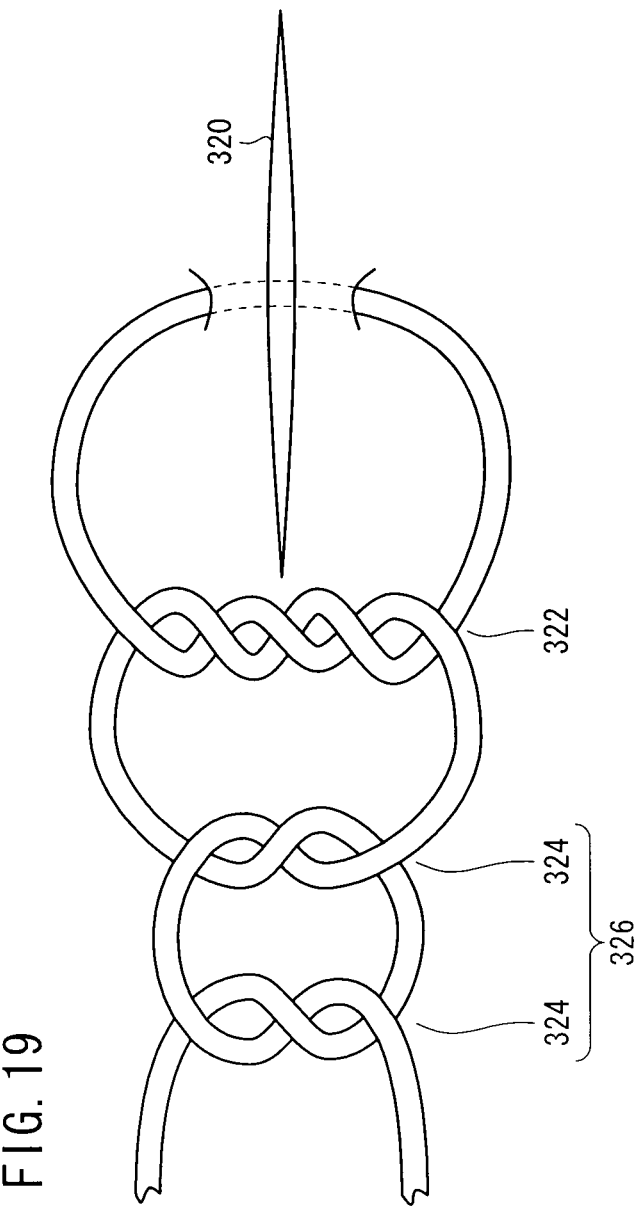
FIG. 19 is a schematic view showing a state in which three loose knots are created.

In step S8, the number of loose knots created by this time is confirmed. If the desired number of loose knots (at least one) has been created, then the suturing and ligating method proceeds to step S9. If the desired number of loose knots has not been formed, then the suturing and ligating method returns to step S3. For example, as shown in FIG. 19, to form one double half knot 322 and two single half knots 324, steps S3 to S7 are carried out three times. Further, it is preferable to change the direction in which the suture strand 314 is wound alternately when steps S3 to S7 are repeated.

Figure 20:
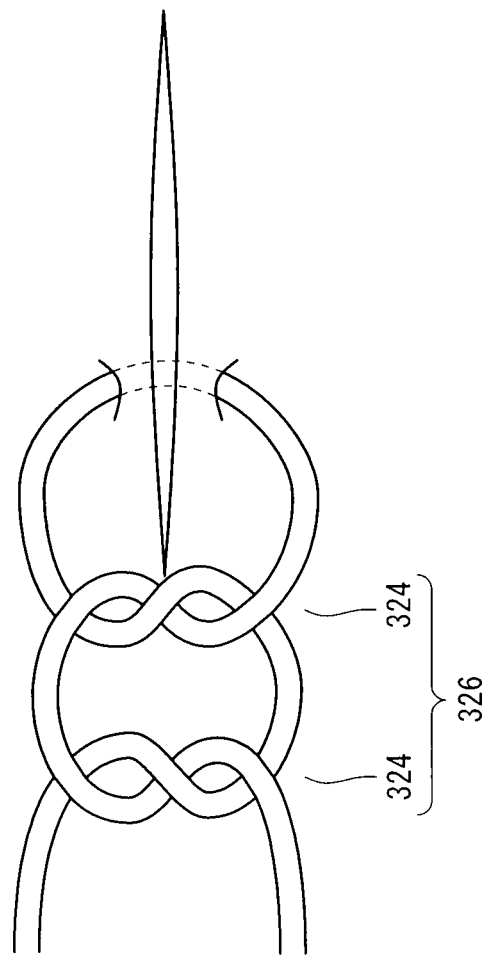
FIG. 20 is a schematic view showing a state in which two loose knots are created.
Figure 21:
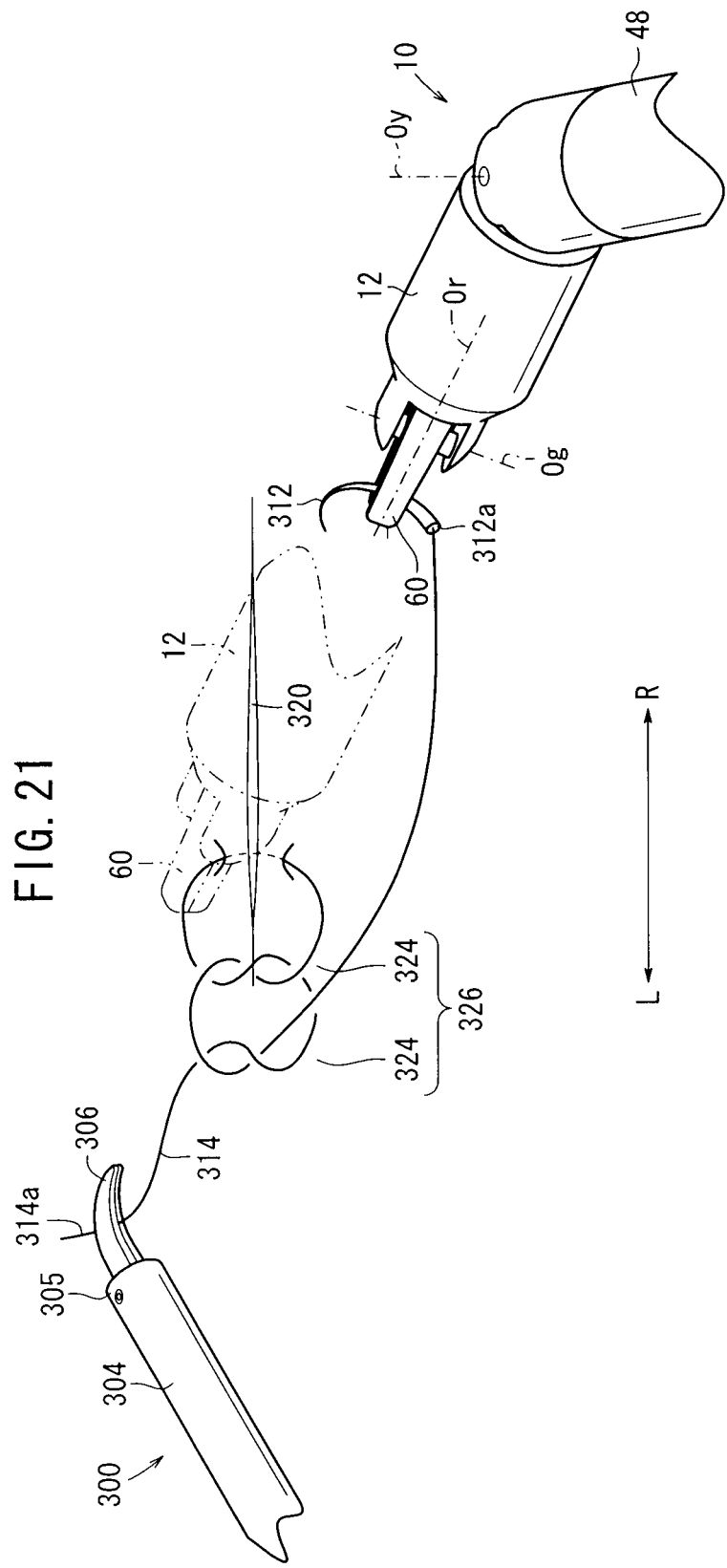
FIG. 21 is a fragmentary perspective view showing a second pulling step of the intracoelomic suturing and ligating method according to the first embodiment.

In the following explanatory example, as shown in FIGS. 20 and 21, the suture strand 314 is wound once around the distal-end working unit 305 in one direction and then wound once again around the distal-end working unit 305 in the direction opposite to the one direction, so that a square knot 326 made up of two single half knots 324 is created.

Figure 22:
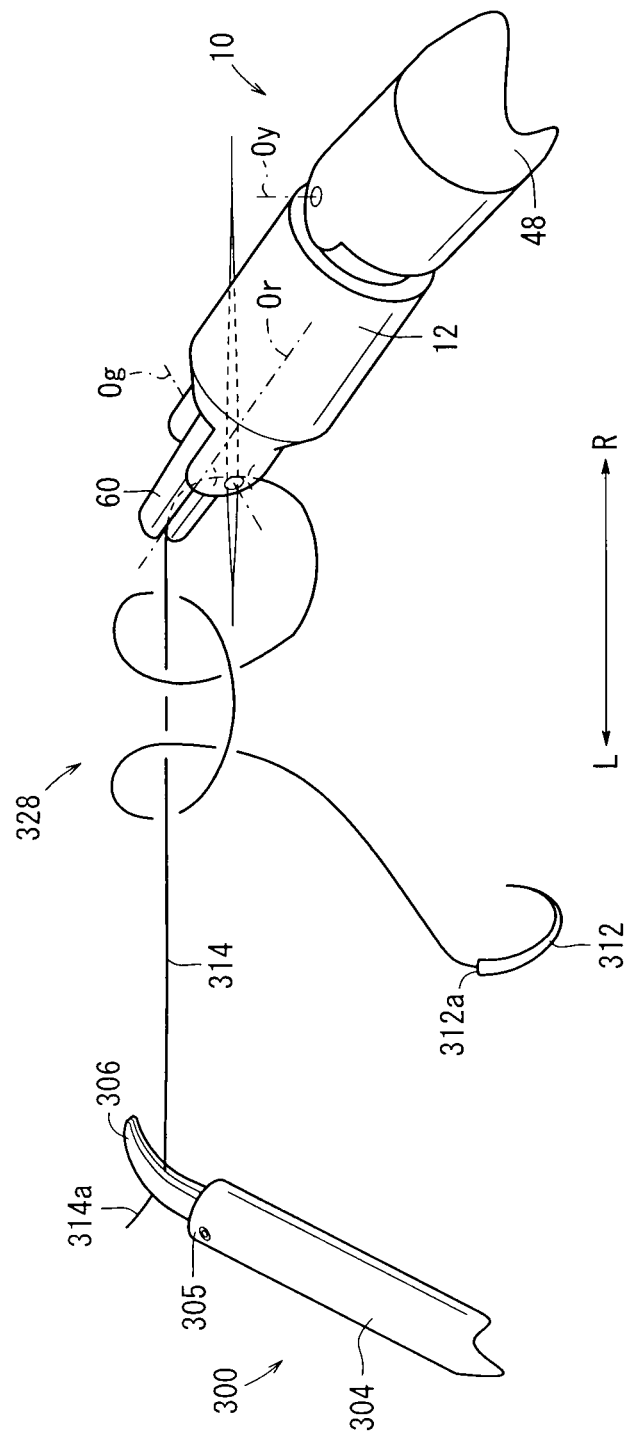
FIG. 22 is a fragmentary perspective view showing a slip knot creating step of the intracoelomic suturing and ligating method according to the first embodiment.

In step S9 (slip knot creating step), the gripper 60 is opened to release the curved needle 312, and then grips a portion of the suture strand 314, which is not inserted into the tissue 320, at a point of the suture strand 314 closer to the tissue 320 than the square knot 326, as shown by imaginary lines in FIG. 21. Next, the distal-end working unit 12 and the distal-end working unit 305 are pulled in opposite directions so that the suture strand 314 between the distal-end working unit 12 and the distal-end working unit 305 becomes straight, as shown in FIG. 22, and thus a slip knot 328 is created.

Figure 23A:
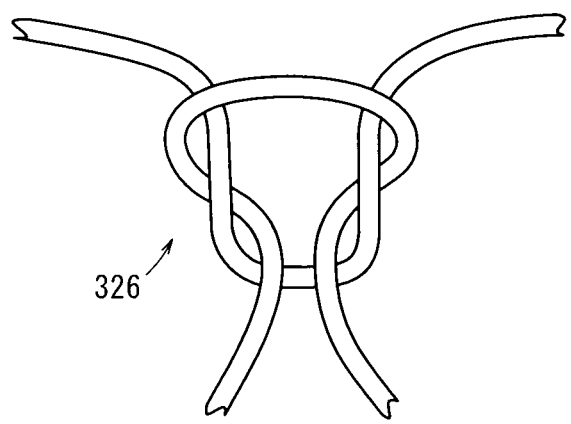
FIG. 23A is a schematic view showing a square knot before converted to the slip knot.
Figure 23B:
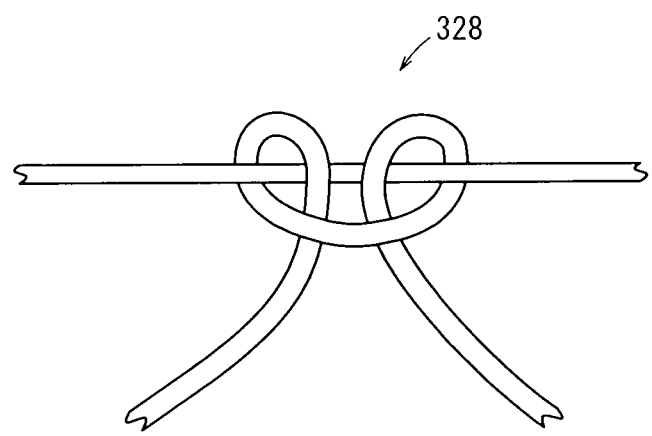
FIG. 23B is a schematic view showing the slip knot converted from the square knot.

Specifically, by pulling the suture strand 314 on one side of the square knot 326 shown in FIG. 23A, the square knot 326 is converted to the slip knot 328 shown in FIG. 23B. At this time, the operator can feel a response and sense the conversion. It is preferable that the grippers 60, 306 grips portions as close to the square knot 326 as possible. As is clear from FIG. 23B, the slip knot 328 can be slidable along the suture strand.

Figure 24:
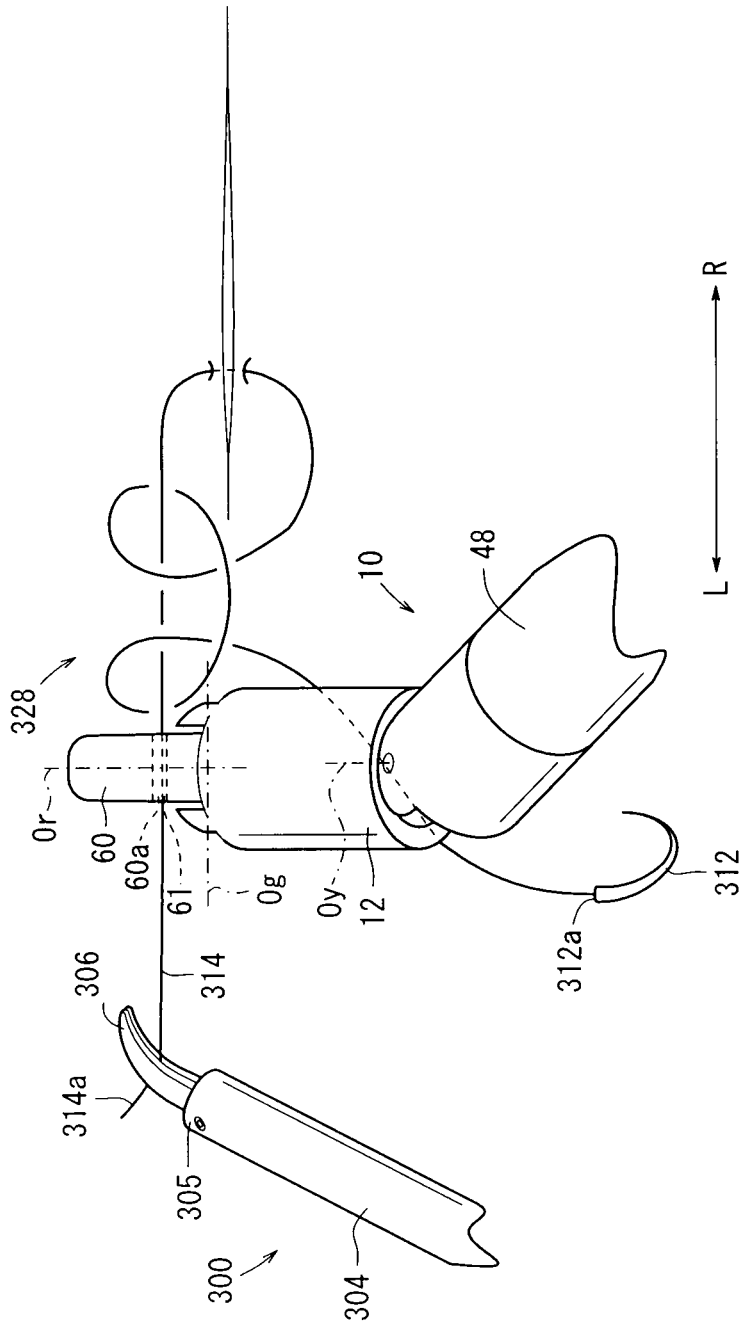
FIG. 24 is a fragmentary perspective view showing a preparatory stage for a sliding step of the intracoelomic suturing and ligating method according to the first embodiment.
Figure 25:
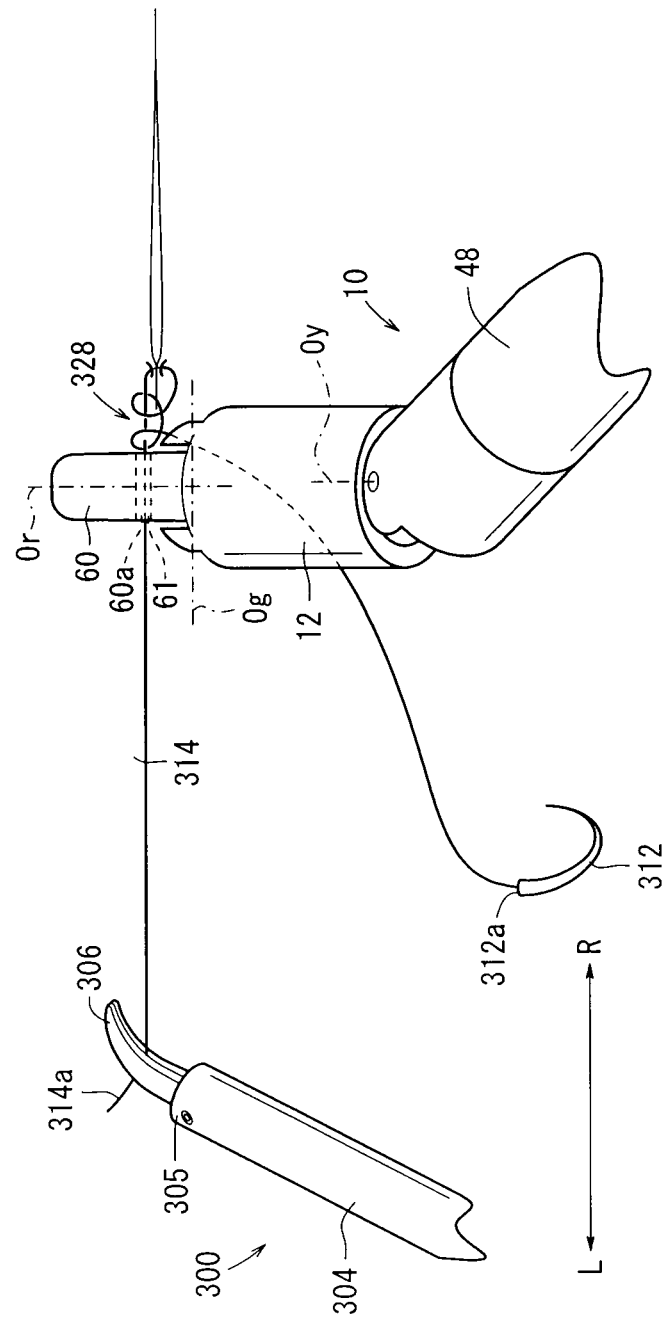
FIG. 25 is a fragmentary perspective view showing the sliding step of the intracoelomic suturing and ligating method according to the first embodiment.

In step S10 (sliding step), the gripper 60 is opened to release the suture strand 314, and then closed such that a portion of the suture strand 314, which is not inserted into the tissue 320, extends through the hole 61 at a point of the suture strand 314 closer to a portion gripped by the gripper 306 than the slip knot 328, as shown in FIG. 24. Next, as shown in FIG. 25, the gripper 60 is moved toward the tissue so as to slide the slip knot 328 closer to the tissue, thereby closing the incision 320.

According to step S10 (and step S110), by using the slidable slip knot 328, the incision 320 can be sufficiently closed.

Figure 26:
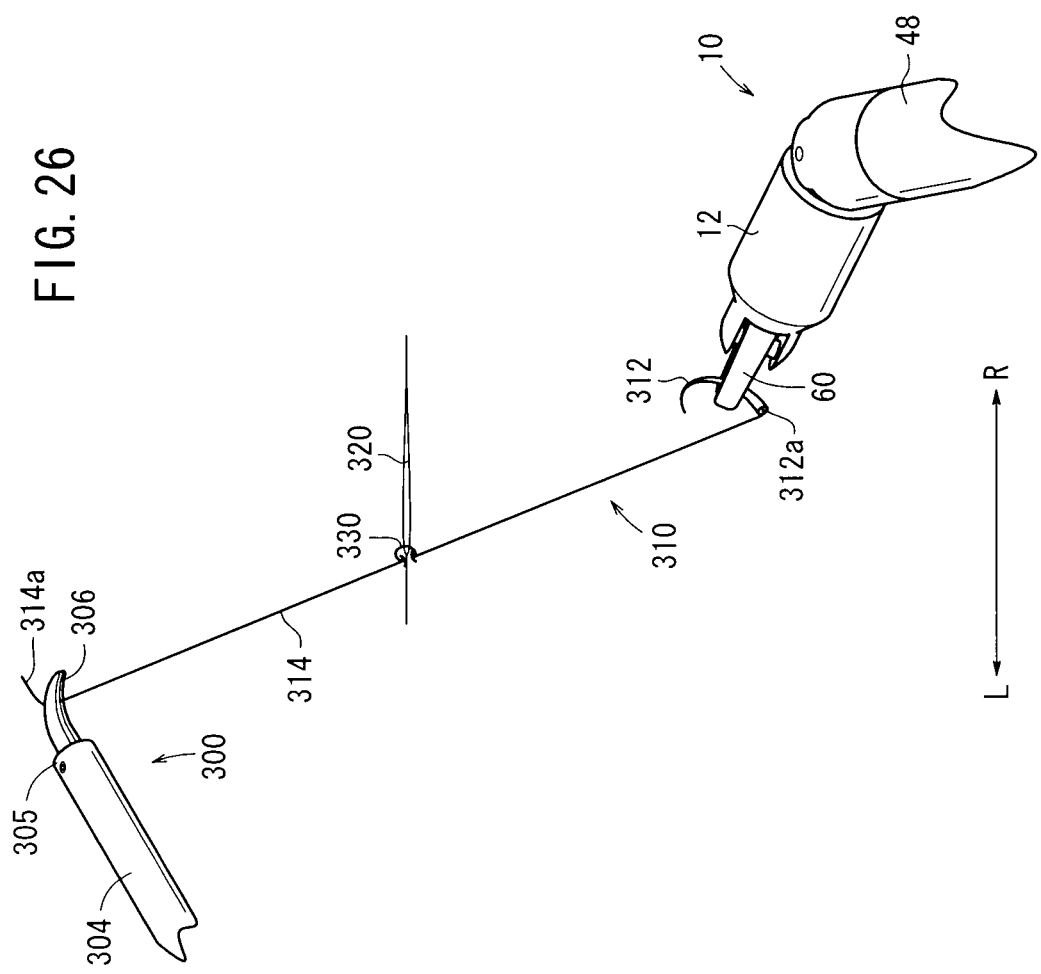
FIG. 26 is a fragmentary perspective view showing a tightening step of the intracoelomic suturing and ligating method according to the first embodiment.

In step S11 (tightening step), as shown in FIG. 26, the distal-end working unit 12 and the distal-end working unit 305 are moved away from each other to thereby form a knot 330 across the incision 320. In step S11 (also in step S111, to be described later), the gripper 60 and the gripper 306 may grip the suture strand 314 at different positions, so that the distal-end working unit 12 and the distal-end working unit 305 are not excessively spaced from each other, and thus allowing the manipulator 10 and the forceps 300 to perform the surgical procedure within a limited space. In step S11, the slip knot 328 is converted to a locking square know 326 which is not loosened.

In steps S7, S9 and S11, the distal-end working unit 12 may be tilted in order to pull the suture strand 314.

Thereafter, if necessary, the processing sequence shown in FIG. 10, except step S, may be carried out at least once in order to reinforce the knot 330. Depending on the size of the incision 320, a plurality of knots 330 may be formed.

With the intracoelomic suturing and ligating method according to the first embodiment, the curved needle 312 is changed in orientation by the rolling mechanism, thereby enabling the suture strand 314 to be easily wound around the distal-end working unit 305 in steps S3 and S4.

At this time, only the distal-end working unit 12 of the manipulator 10 is swung by the rolling mechanism, whereas the forceps 300 is swung or moved back and forth while the distal-end working unit 12 is swung or remains substantially unmoved. Since the distal-end working unit 12 and the forceps 300 are required to move only by small distances, they can be used within limited regions inside the body cavity. In addition, the length of the suture strand 314, which extends through the incision 320, may be shorter than has heretofore been possible, and hence, the distal-end working unit 12 and the forceps 300 are less susceptible to the natural tendency of the suture strand 314.

The manipulator 10 basically is required to operate about one axis, by orienting the rolling mechanism alternately with respect to the U direction and the D direction. Therefore, it is easy to train an operator to use the manipulator 10.

With the intracoelomic suturing and ligating method according to the first embodiment, the manipulator 10 is operated mainly by rolling the distal-end working unit 12 and by opening and closing the gripper 60. Therefore, the tilting mechanism of the manipulator 10 is not an essential element.

In step S2, the suture strand 314 is positioned in front of the distal-end working unit 305, i.e., more closely to the operator. However, if desired, the suture strand 314 may be positioned behind the distal-end working unit 305. In this case, the distal-end working unit 12 and the distal-end working unit 305 may subsequently be moved relative to each other inversely in steps S3 and S4.

An intracoelomic suturing and ligating method according to a second embodiment of the present invention, which is carried out using the manipulator 10 and the forceps 300, shall be described below with reference to FIG. 27.

The intracoelomic suturing and ligating method according to the second embodiment is performed after a certain preparatory process and a given surgical technique have been carried out, by inserting the manipulator 10 and the forceps 300 through respective trocars 20 into a body cavity during an endoscopic surgical operation. The operator, typically a surgeon, performs the intracoelomic suturing and ligating method while watching images captured by an endoscope, not shown.

Figure 27:
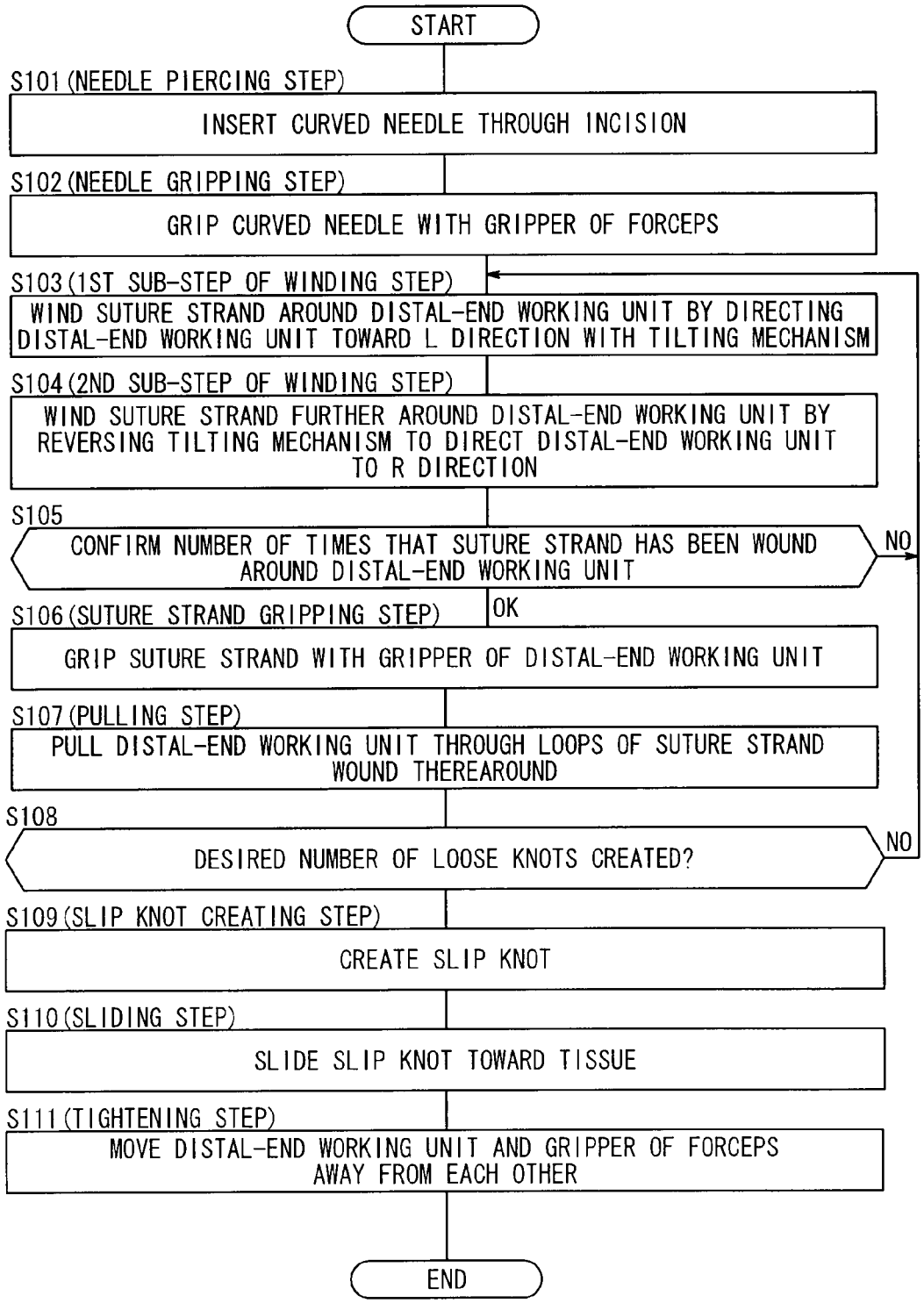
FIG. 27 is a flowchart of a sequence of an intracoelomic suturing and ligating method according to a second embodiment of the present invention.

Step 101 (needle piercing step) shown in FIG. 27 is identical to step S1 described above.

Figure 28:
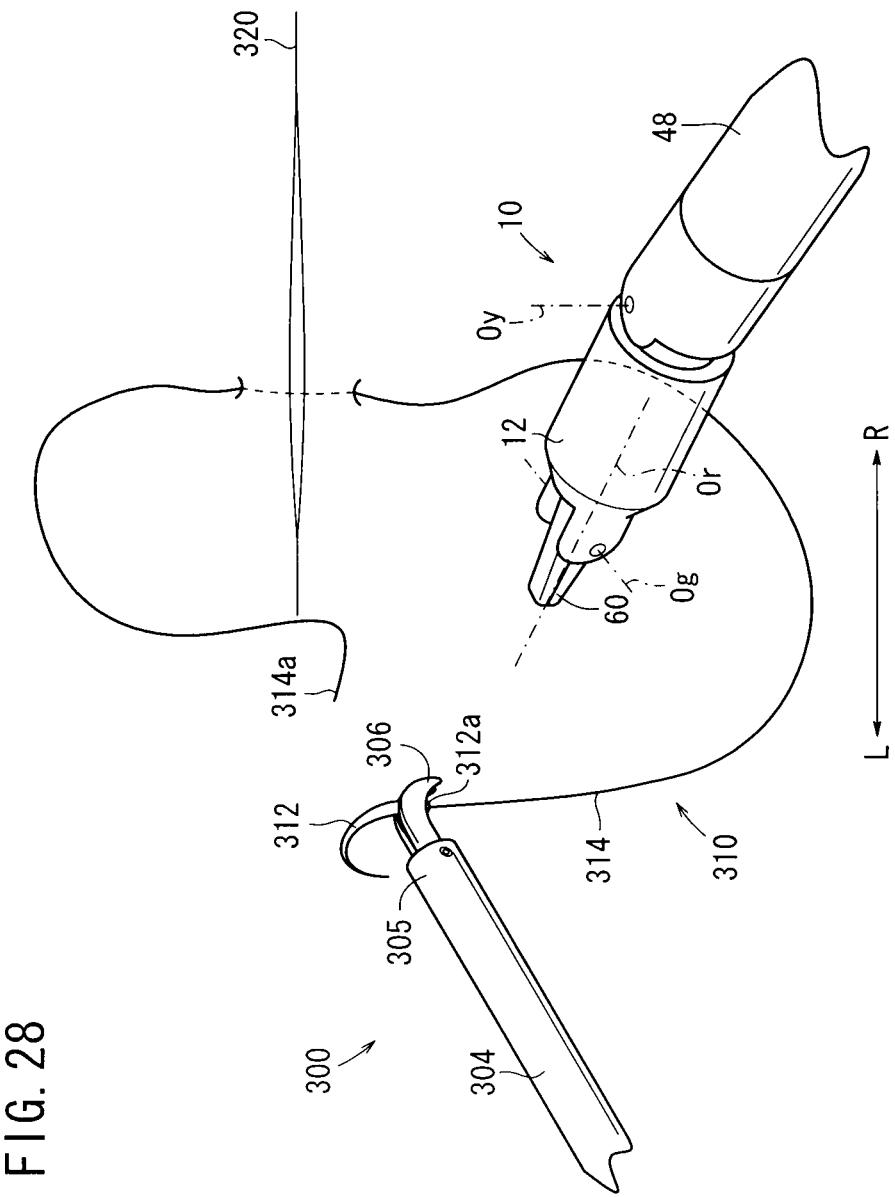
FIG. 28 is a fragmentary perspective view showing a needle gripping step of the intracoelomic suturing and ligating method according to the second embodiment.

In step S102 (needle gripping step), as shown in FIG. 28, the gripper 306 grips the curved needle 312. At this time, the gripper 306 may also grip a length of the suture strand 314, which is inserted through the incision 320, rather than gripping the curved needle 312. However, gripping the curved needle 312 will make subsequent surgical procedures more stable within the body cavity. Subsequently, the gripper 306 continues to grip the curved needle 312, until one suturing cycle has been completed. At this time, the suture strand 314 passes underneath the distal-end working unit 12. The distal-end working unit 12 is disposed slightly below the distal-end working unit 305.

In preparation for following steps S103 and S104 (winding step), the gripper 60 around which the suture strand 314 will be wound remains closed, so that the suture strand 314 is less liable to become entangled with the distal-end working unit 12, and can easily be coiled around the distal-end working unit 12.

Figure 29:
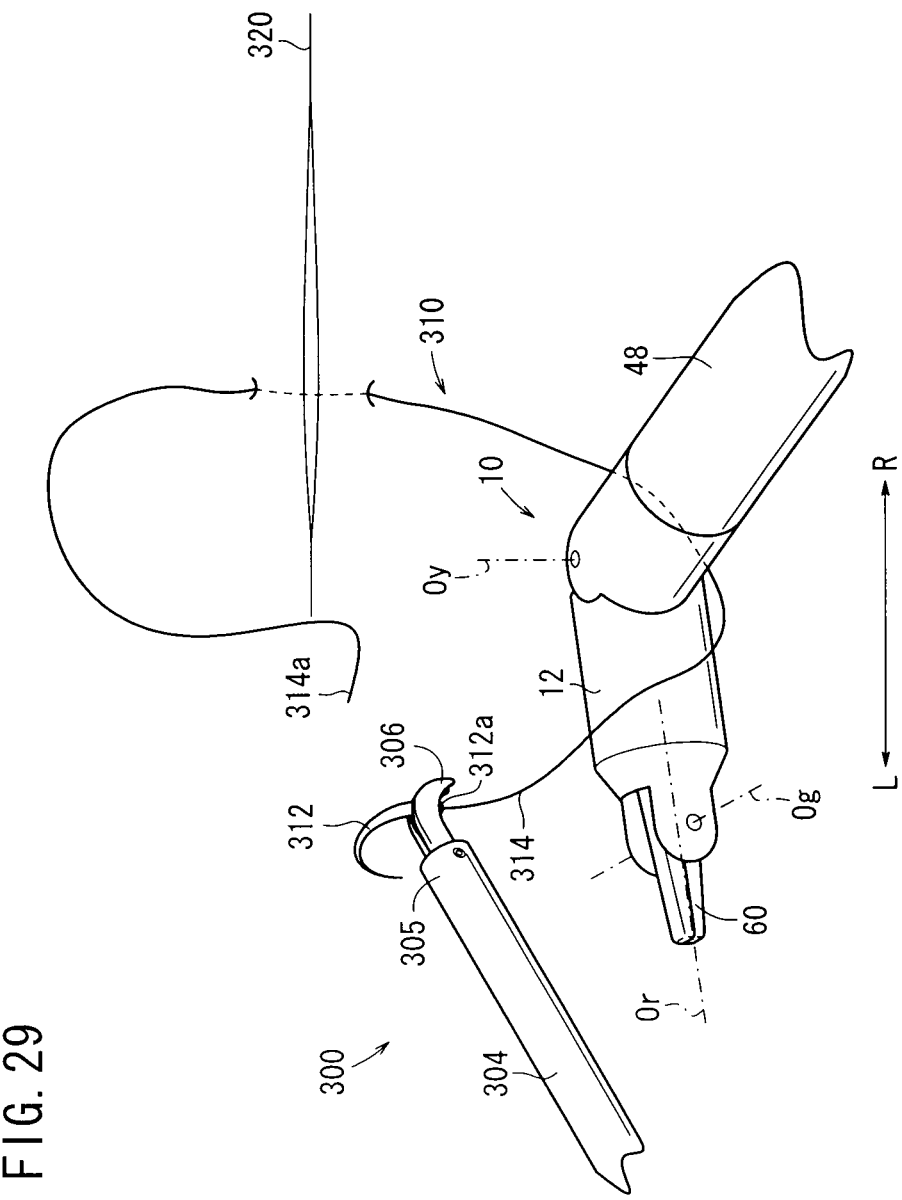
FIG. 29 is a fragmentary perspective view showing a first sub-step of a winding step of the intracoelomic suturing and ligating method according to the second embodiment.

In step S103 (first sub-step), as shown in FIG. 29, the tilting mechanism is actuated to tilt the distal-end working unit 12 toward the other distal-end working unit 305, i.e., in the L direction, thereby winding the suture strand 314 around a lower portion of the distal-end working unit 12 by about one-half turn.

In step S103, the suture strand 314 is made to pass from a central portion of the distal-end working unit 12 substantially over the gripper 60. The distal-end working unit 12 may be disposed slightly below the distal-end working unit 305, so that the gripper 60 may be moved toward the operator from a position directly beneath the gripper 306.

Figure 30:
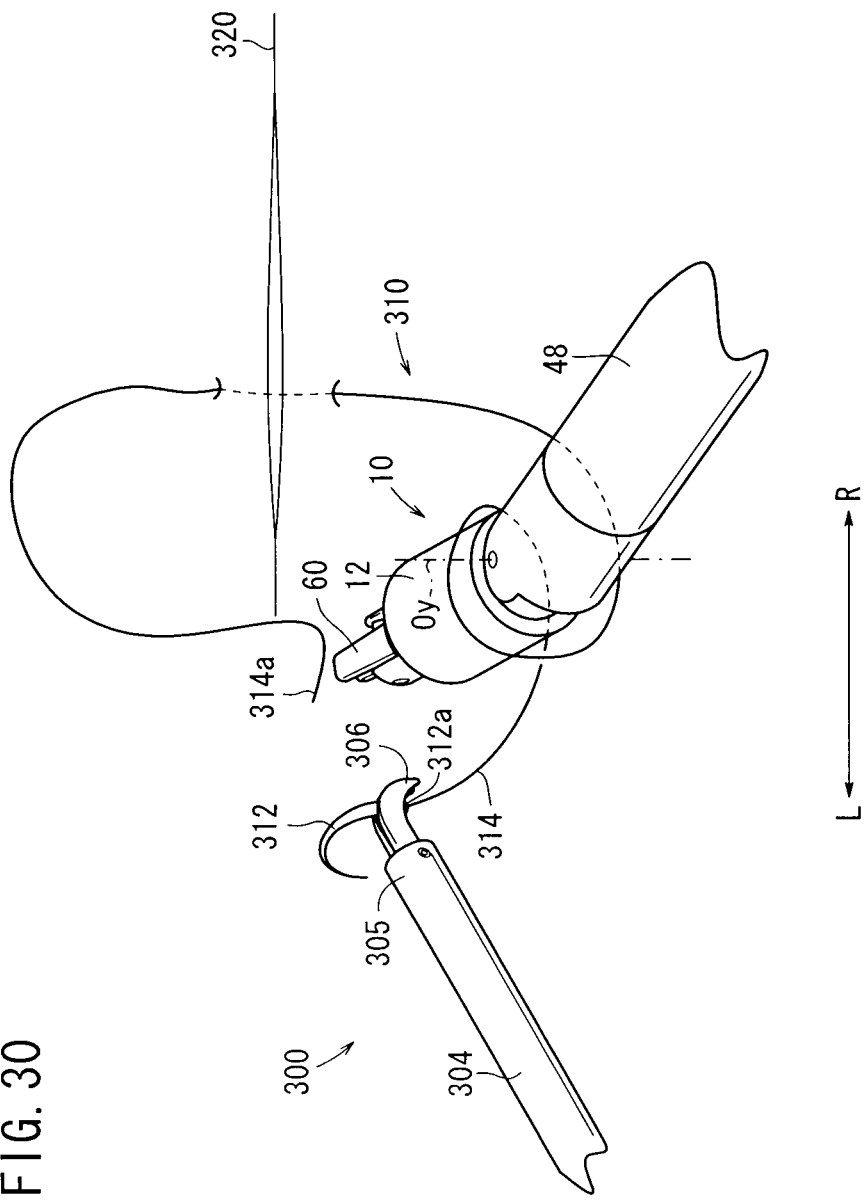
FIG. 30 is a fragmentary perspective view showing a second sub-step of the winding step of the intracoelomic suturing and ligating method according to the second embodiment.

In step S104 (second sub-step), as shown in FIG. 30, the tilting mechanism is reversed in order to tilt the distal-end working unit 12 away from the distal-end working unit 305, i.e., in the R direction, thereby winding the suture strand 314 further around the distal-end working unit 12 by about one-half turn. The suture strand 314 is now wound around the distal-end working unit 305 by a full turn.

In step S104, the distal-end working unit 12 may be tilted while being moved slightly upwardly of the distal-end working unit 305, or the distal-end working unit 12 may be tilted while moving the distal-end working unit 305 slightly downwardly of the distal-end working unit 12, to thereby wind the suture strand 314 around an upper portion of the distal-end working unit 12.

In steps S103 and S104, the above-mentioned movements of the distal-end working unit 12 can be achieved by alternately pushing the left and right surfaces 133a, 133b (see FIG. 4) of the pad 132 with the operator's finger (thumb). The pad 132 as the pushing input means, which controls the tilting mechanism of the distal-end working unit 12, allows the operator to operate the manipulator 10 intuitively through a simple process.

When step S103 and step S104 are performed, the distal-end working unit 305 may be moved back and forth with respect to the gripper 60 of the other distal-end working unit 12, or alternatively, the distal-end working unit 12 may be vertically displaced relative to the gripper 306, for easily winding the suture strand 314 around the distal-end working unit 12. For sufficiently tilting the distal-end working unit 12, a difference between the angular displacement of the tilting mechanism at the time of step S103 and the angular displacement of the tilting mechanism at the time of step S104 should preferably be about 80°. Actually, however, the difference between the angular displacements may be varied within a range from about 60° to 90°, for sufficiently tilting the distal-end working unit 12.

In step S105, the operator confirms the number of times that the suture strand 314 has been wound around the distal-end working unit 12. If the suture strand 314 has been wound around the distal-end working unit 12 a predetermined number of times (once or more, e.g., twice), then the intracoelomic suturing and ligating method proceeds to step S106. If the suture strand 314 has not been wound the predetermined number of times around the distal-end working unit 305, then the intracoelomic suturing and ligating method returns to step S104. Step S105 is similar to step S5 described above.

Figure 31:
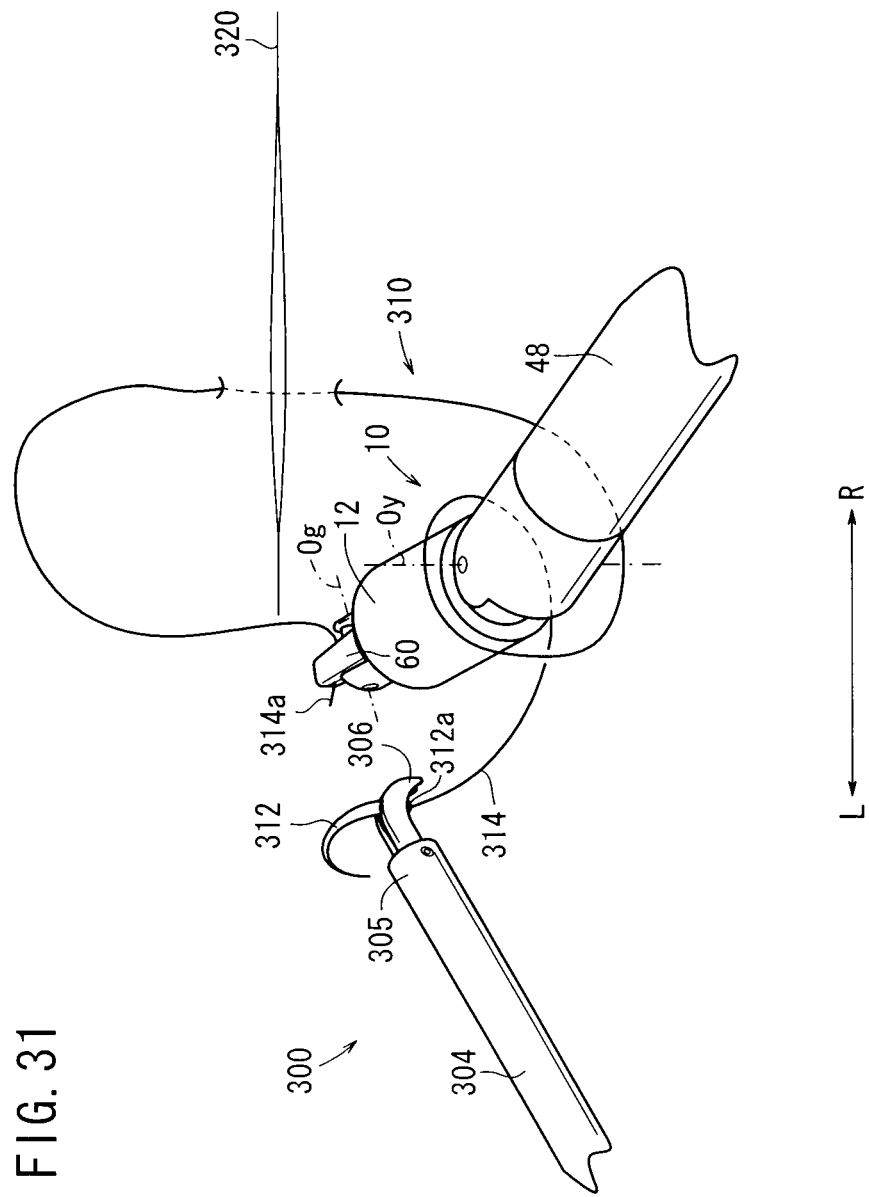
FIG. 31 is a fragmentary perspective view showing a suture strand gripping step of the intracoelomic suturing and ligating method according to the second embodiment.

In step S106 (suture strand gripping step), the gripper 306 is opened. Then, as shown in FIG. 31, the gripper 306 is closed again to grip a portion (e.g., the end portion 314a) of the suture strand 314, which has not been inserted into the tissue.

Figure 32:
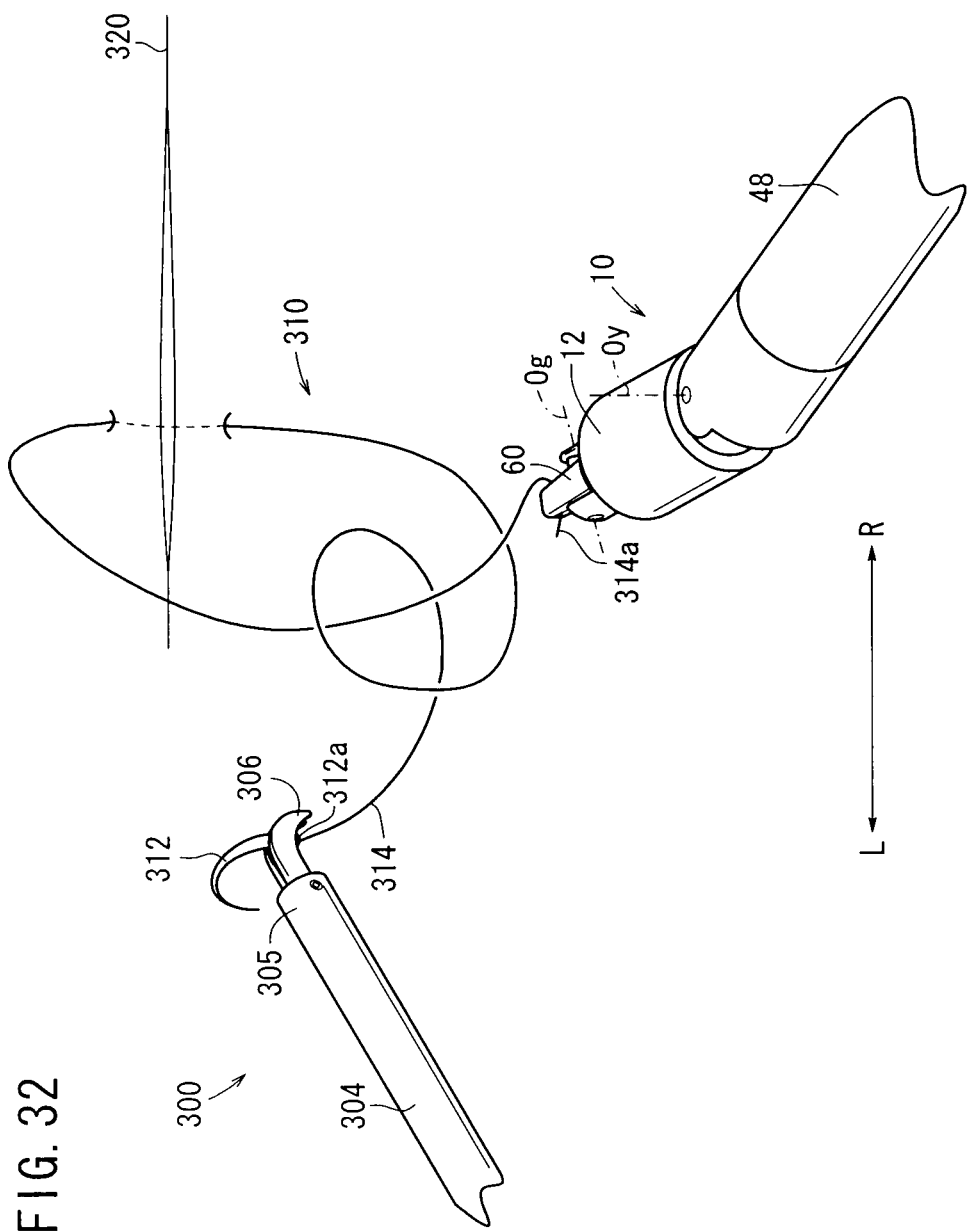
FIG. 32 is a fragmentary perspective view showing a pulling step of the intracoelomic suturing and ligating method according to the second embodiment.

In step S107 (pulling step), as shown in FIG. 32, the manipulator 10 is pulled toward the operator, and the distal-end working unit 305 is pushed away from the operator, thereby withdrawing the gripper 60 through the loops of the suture strand 314, which have been wound around the distal-end working unit 12. Depending on conditions within the body cavity, the manipulator 10 may either be pulled toward the operator, or the distal-end working unit 305 may be pushed away from the operator.

In step S108, the number of loose knots created by this time is confirmed. If the desired number of loose knots has been created, then the suturing and ligating method proceeds to step S109. If the desired number of loose knots has not been created, then the suturing and ligating method returns to step S103. This step S108 is identical to step S8 above. In the following explanatory example, as shown in FIGS. 20 and 33, a square knot 326 made up of two single half knots 324 is created.

Figure 33:
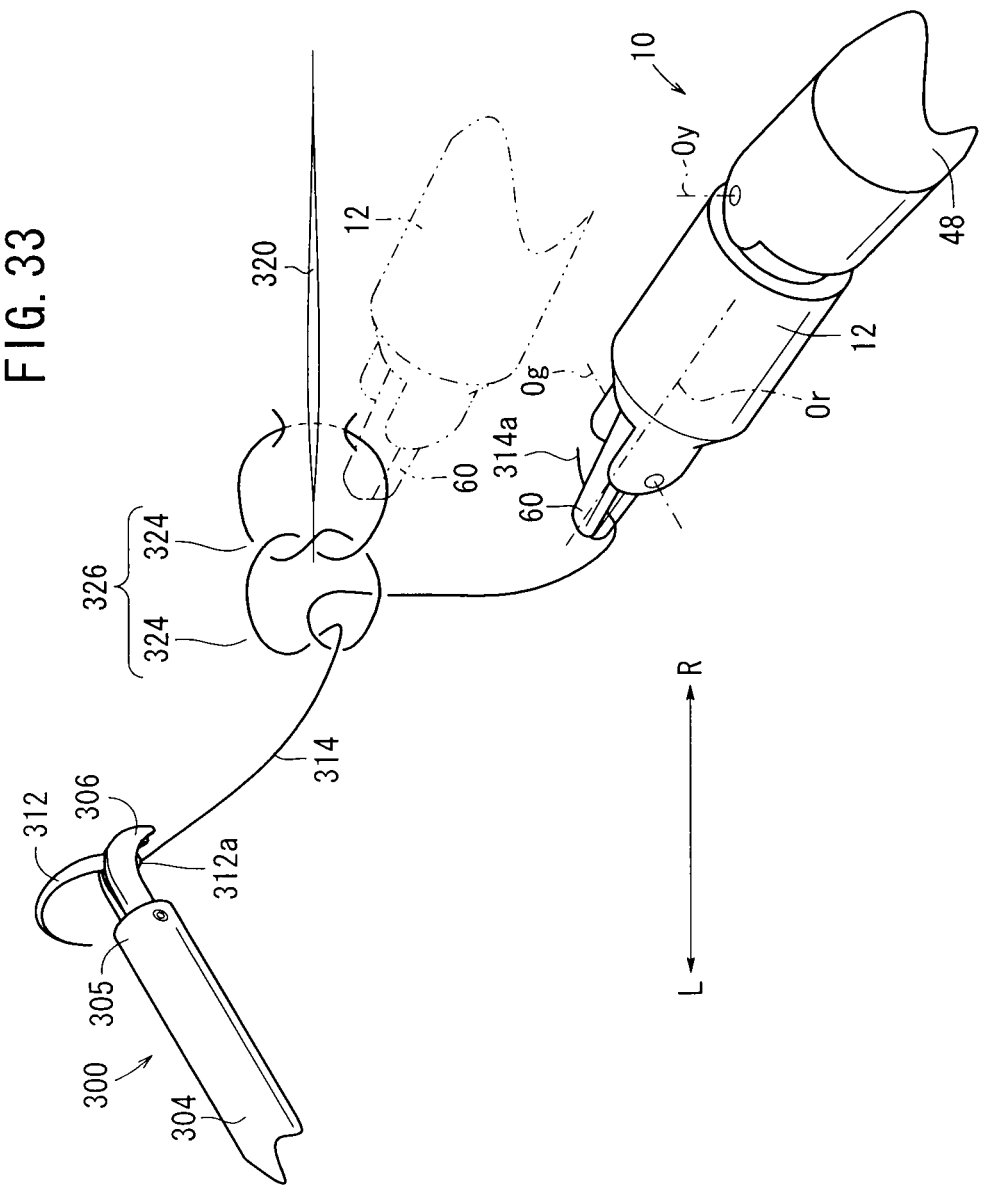
FIG. 33 is a fragmentary perspective view showing a second pulling step of the intracoelomic suturing and ligating method according to the second embodiment.
Figure 34:
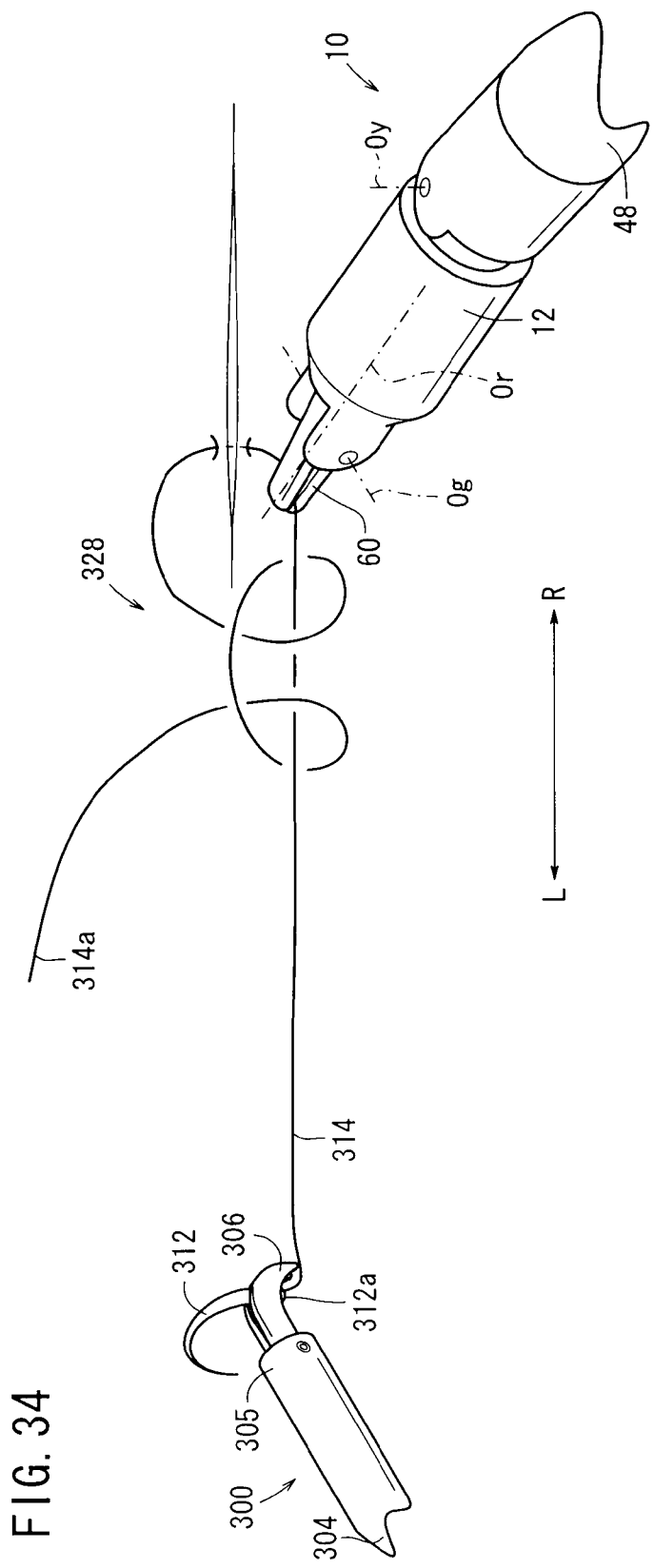
FIG. 34 is a fragmentary perspective view showing a slip knot creating step of the intracoelomic suturing and ligating method according to the second embodiment.

In step S109 (slip knot creating step), the gripper 60 is opened to release the suture strand 314, and then grips a portion of the suture strand 314, which is inserted into the tissue 320, at a point of the suture strand 314 closer to the tissue 320 than the square knot 326, as shown by imaginary lines in FIG. 33. Next, the distal-end working unit 12 and the distal-end working unit 305 are pulled in opposite directions so that the suture strand 314 between the distal-end working unit 12 and the distal-end working unit 305 becomes straight, as shown in FIG. 34, and thus a slip knot 328 is created.

Figure 35:
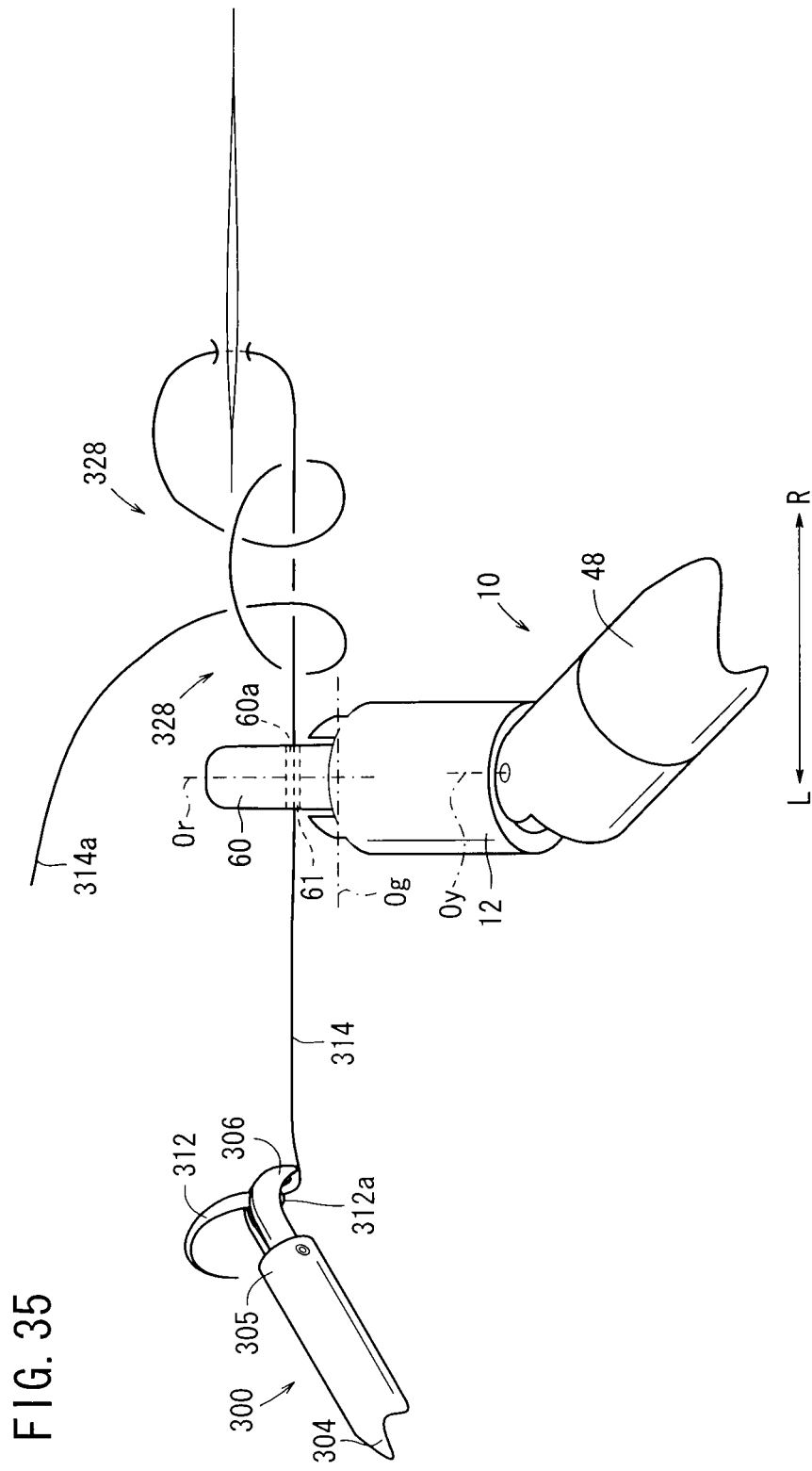
FIG. 35 is a fragmentary perspective view showing a preparatory stage for a sliding step of the intracoelomic suturing and ligating method according to the second embodiment.
Figure 36:
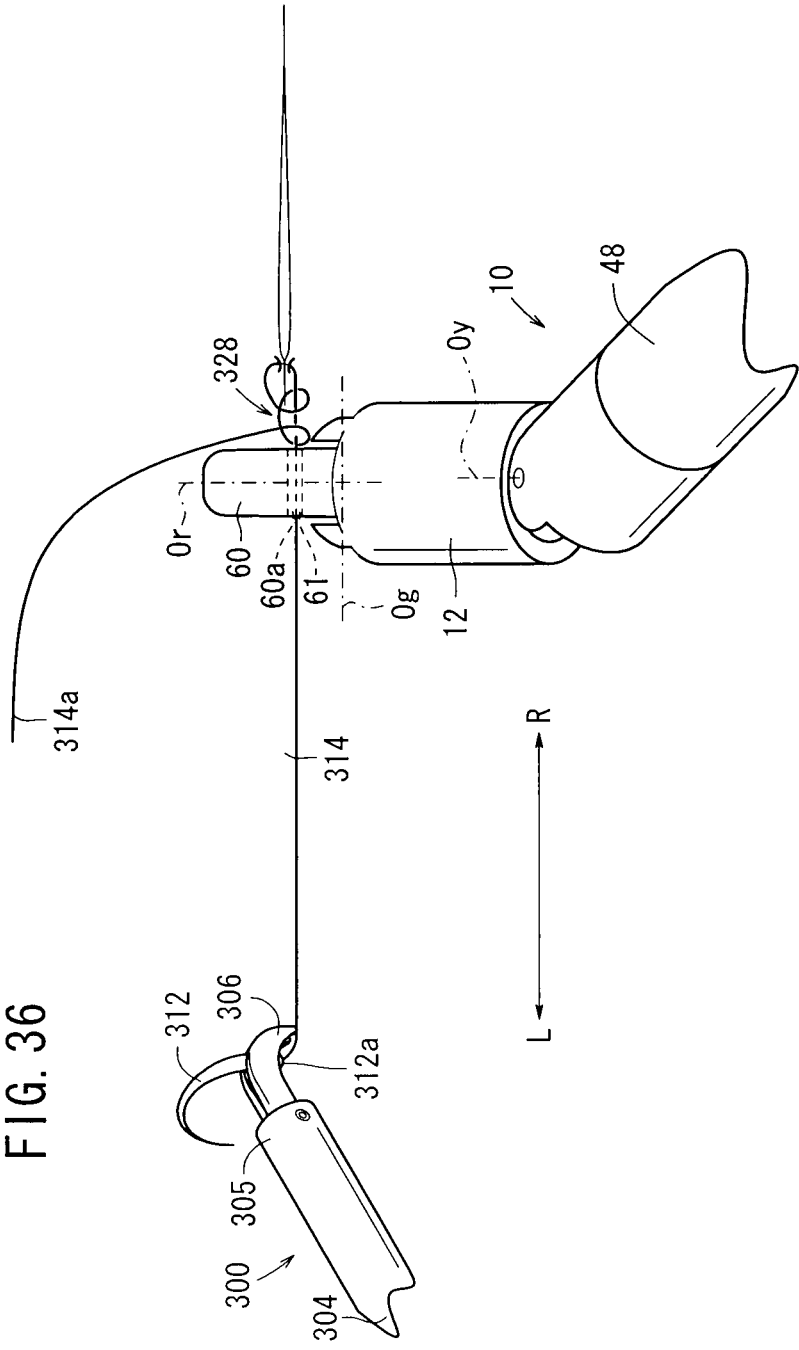
FIG. 36 is a fragmentary perspective view showing the sliding step of the intracoelomic suturing and ligating method according to the second embodiment.

In step S110 (sliding step), the gripper 60 is opened to release the suture strand 314, and then closed such that a portion of the suture strand 314, which is inserted into the tissue 320, extends through the hole 61 at a point of the suture strand 314 closer to a portion gripped by the gripper 306 than the slip knot 328, as shown in FIG. 35. Next, as shown in FIG. 36, the gripper 60 is moved toward the tissue so as to slide the slip knot 328 closer to the tissue, thereby closing the incision 320.

Figure 37:
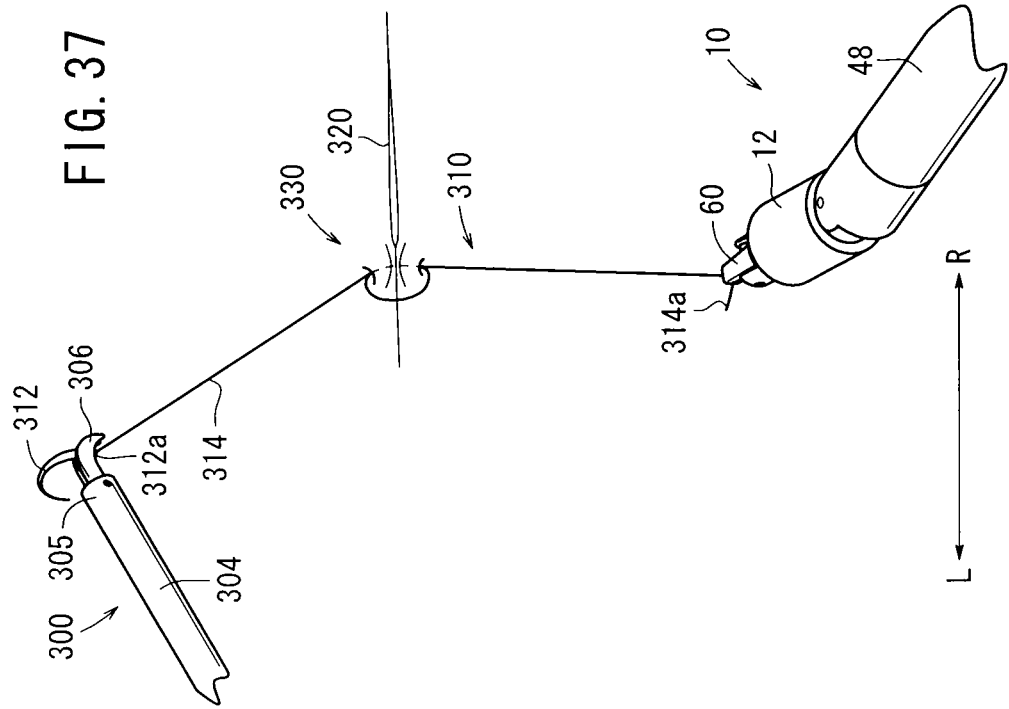
FIG. 37 is a fragmentary perspective view showing a tightening step of the intracoelomic suturing and ligating method according to the second embodiment.
Figure 38:
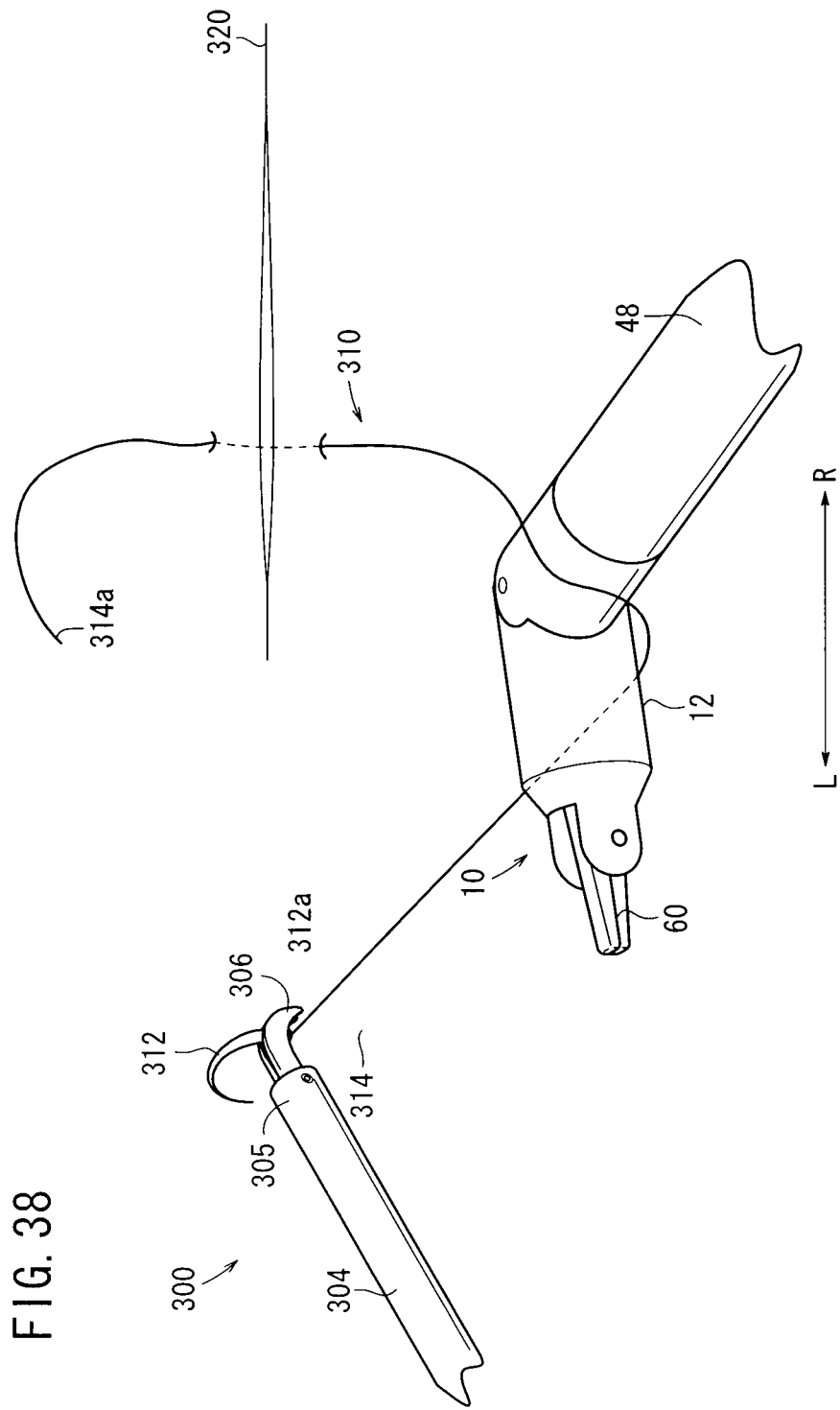
FIG. 38 is a fragmentary perspective view showing an initial state of an intracoelomic suturing and ligating method, according to a first modification of the second embodiment.
Figure 39:
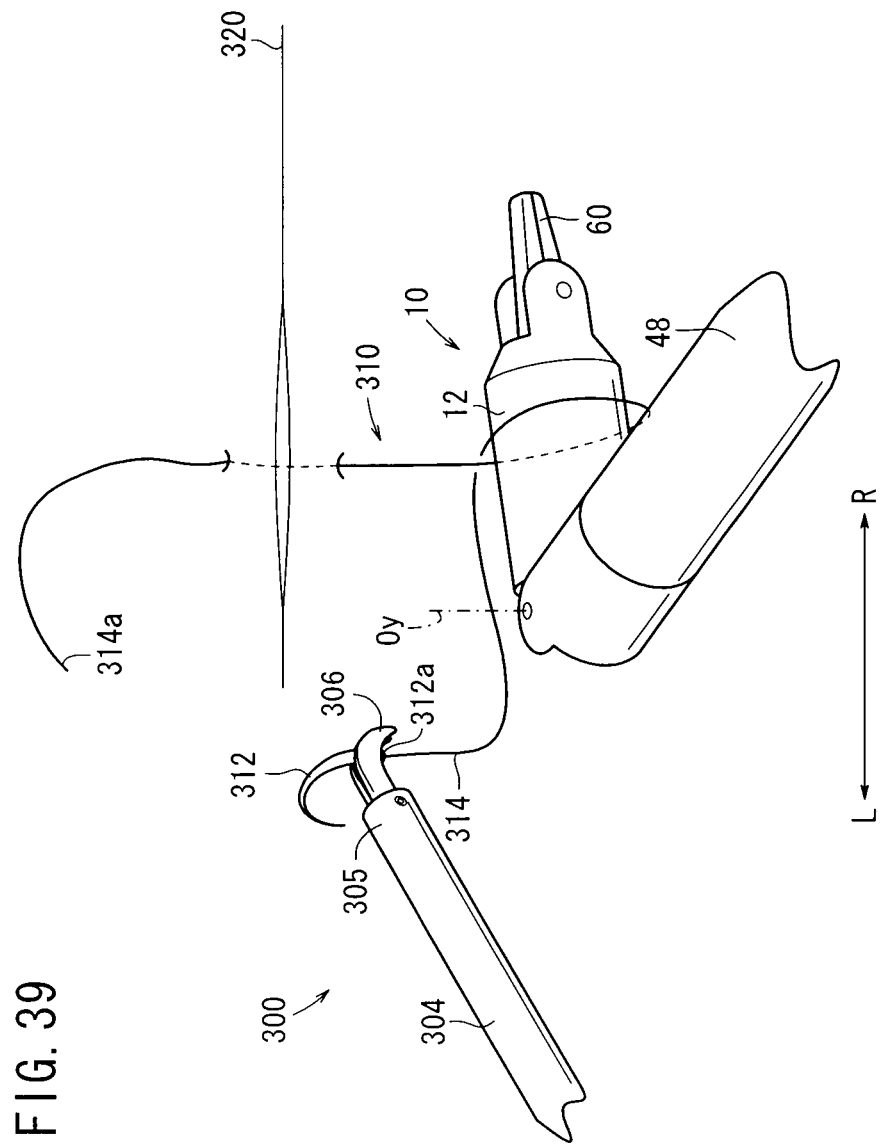
FIG. 39 is a fragmentary perspective view showing an intermediate state of the intracoelomic suturing and ligating method according to the first modification of the second embodiment.

In step S111 (tightening step), as shown in FIG. 37, the distal-end working unit 12 and the distal-end working unit 305 are moved away from each other, so as to form a knot 330 across the incision 320.

Thereafter, if necessary, the processing sequence shown in FIG. 27, except step S101, may be carried out at least once to reinforce the knot 330. Depending on the size of the incision 320, a plurality of knots 330 may be formed.

In steps S107, S109 and S111, the distal-end working unit 12 may be tilted to pull the suture strand 314.

With the intracoelomic suturing and ligating method according to the second embodiment, the distal-end working unit 12 is changed in orientation by the tilting mechanism, so as to wind the suture strand 314 easily around the distal-end working unit 12 in steps S103 and S104.

At this time, only the distal-end working unit 12 of the manipulator 10 is swung by the tilting mechanism, and the forceps 300 is swung or moved back and forth as the distal-end working unit 12 is swung or remains substantially unmoved. Since the distal-end working unit 12 and the forceps 300 are required to move only by small distances, they can be used within limited regions inside the body cavity. In addition, the length of the suture strand 314, which extends through the incision 320, may be shorter than was heretofore possible. Thus, the distal-end working unit 12 and the forceps 300 are less susceptible to the natural tendency of the suture strand 314.

The manipulator 10 basically is required to operate about one axis by orienting the tilting mechanism alternately to the L direction and the R direction. Therefore, it is easy to train an operator to use the manipulator 10.

With the intracoelomic suturing and ligating method according to the second embodiment, the manipulator 10 is operated mainly by tilting the distal-end working unit 12 and by opening and closing the gripper 60. Therefore, the rolling mechanism of the manipulator 10 is not an essential element.

In step S102, the suture strand 314 passes below the distal-end working unit 12. However, the suture strand 314 may also be positioned above the distal-end working unit 12. In this case, the distal-end working unit 12 is tilted in the L direction, as indicated by the solid line in FIG. 38 in step S103, and then the distal-end working unit 12 is tilted in the R direction, as indicated by the solid line in FIG. 39, to wind the suture strand 314 around the distal-end working unit 12 in step S104.

Figure 40:
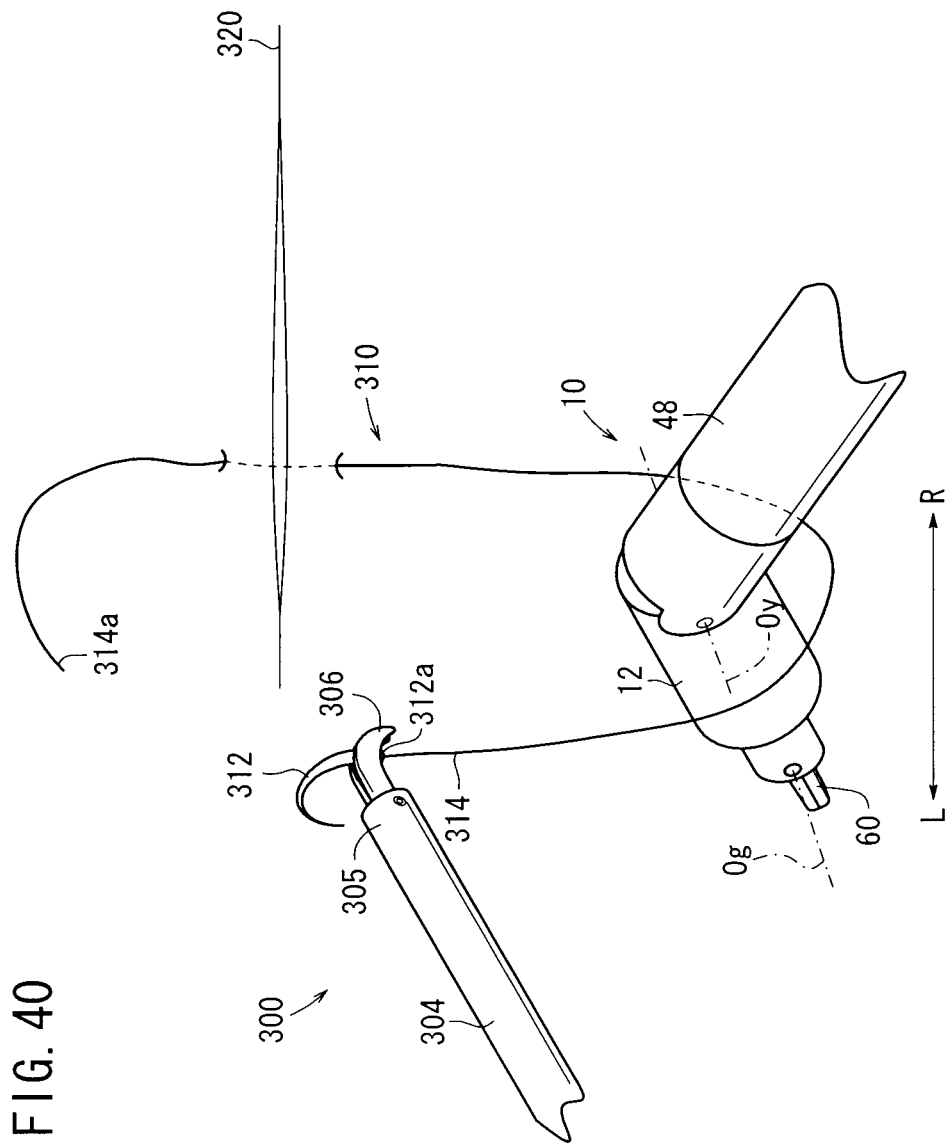
FIG. 40 is a fragmentary perspective view showing an initial state of an intracoelomic suturing and ligating method according to a second modification of the second embodiment.
Figure 41:
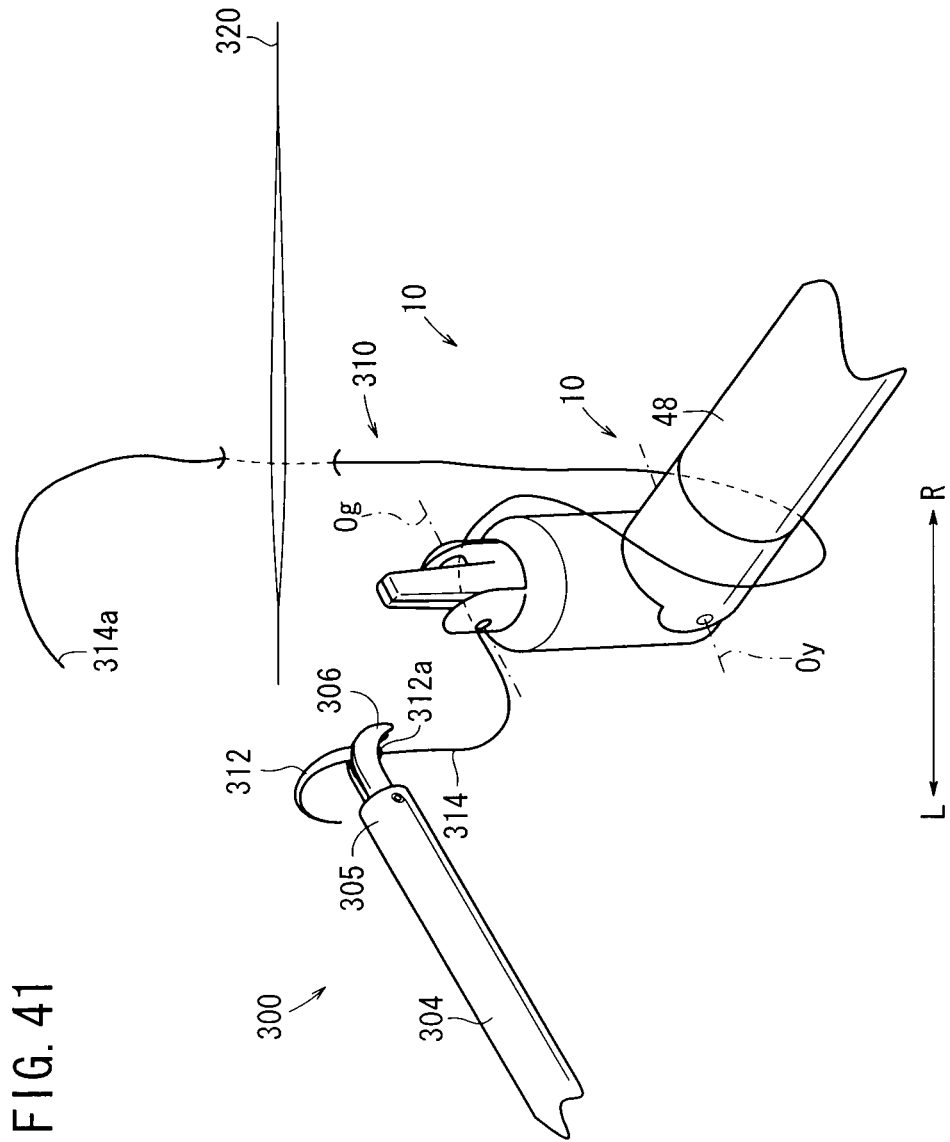
FIG. 41 is a fragmentary perspective view showing an intermediate state of the intracoelomic suturing and ligating method according to the second modification of the second embodiment.

In steps S103 and S104, the distal-end working unit 12 is tilted in lateral directions. However, the manipulator 10 may be tilted through 90°, and then, as shown in FIGS. 40 and 41, the distal-end working unit 12 may be tilted back and forth in vertical directions. Specifically, the distal-end working unit 12 may be tilted back and forth between a lower position, as shown in FIG. 40, and an upper position, as shown in FIG. 41, to wind the suture strand 314 around the distal-end working unit 12. Alternatively, in steps S103 and S104, the distal-end working unit 12 may be tilted in oblique directions rather than in lateral or vertical directions.

In steps S3 and S4, as well as in steps S103 and S104, the manipulator 10 per se may be twisted about the joint shaft 48 in order to change the orientation of the distal-end working unit 12.

In steps S3 and S4, as well as in steps S103 and S104, the distal-end working unit 305 and the distal-end working unit 12 operate while changing relative positions therebetween. However, the distal-end working unit 305 may be fixed in position, whereas the distal-end working unit 12 may be moved back and forth, such that the distal-end working unit 12 mainly is moved. In this case, the operator finds it easy to operate the manipulator 10, because the operator essentially is required to move the dominant hand only.

The intracoelomic suturing and ligating methods according to the first and second embodiments have been illustrated as being applied to suturing procedures. However, the intracoelomic suturing and ligating methods according to the first and second embodiments may also be applied to perform a ligation treatment for a fissure or vessel, e.g., a DVC (Dorsal Vain Complex) ligation in a prostatectomy.

Although certain preferred embodiments of the present invention have been shown and described in detail, it should be understood that various changes and modifications may be made to the embodiments without departing from the scope of the invention as set forth in the appended claims.

What is claimed is:

1. A suturing and ligating method to be performed inside a body cavity within a living body, using a first manipulator which has a first distal-end working unit including a rolling mechanism and a first opening and closing mechanism, and a second manipulator which has a second distal-end working unit including a second opening and closing mechanism, the first manipulator including an operating unit to be held by an operator, the operating unit including a rotary input unit and a motor, wherein the rotary input unit is operable by an operator's finger to supply a rotational command, the motor operating based on input to the rotary input unit, and the rolling mechanism being energized by the motor, the method comprising:

a needle piercing step of inserting a needle of a suture-needle assembly through a tissue in the body cavity while leaving a portion of a suture strand of the suture-needle assembly uninserted in the tissue;

a needle gripping step of gripping the needle with the first opening and closing mechanism;

a winding step of winding the suture strand around the second distal-end working unit of the second manipulator a predetermined number of times by rolling the first opening and closing mechanism of the first manipulator, which is gripping the needle, around a longitudinal axis of the first distal-end working unit in a first rolling direction and then in a second rolling direction opposite to the first rolling direction via the rolling mechanism, so as to reciprocally turn a proximal end portion of the needle for changing orientation of the needle point;

a suture strand gripping step of gripping the portion of the suture strand, which is not inserted into the tissue, with the second opening and closing mechanism;

a pulling step of pulling the portion of the suture strand through loops of the suture strand, which are wound around the second distal-end working unit; and a tightening step of forming a knot by moving the first distal-end working unit and the second distal-end working unit in opposite directions from each other;

wherein, in the winding step, in a state where the suture strand is being wound around the second distal-end working unit, the first opening and closing mechanism gripping the needle is rotated alternately in the first rolling direction and in the second rolling direction.

2. A suturing and ligating method according to claim 1, wherein the winding step further comprises:

a first sub-step of winding the suture strand around the second distal-end working unit a predetermined number of times, by turning the proximal end portion of the needle toward the first rolling direction with the rolling mechanism; and a second sub-step of winding the suture strand further around the second distal-end working unit, by turning the proximal end portion of the needle with the rolling mechanism, in the second rolling direction;

wherein the first sub-step and the second sub-step are performed at least once.

3. A suturing and ligating method according to claim 1, wherein the first distal-end working unit includes a tilting mechanism, at least the winding step comprising the step of tilting the first distal-end working unit with the tilting mechanism, in a direction from a central axis of the shaft of the first manipulator toward the second distal-end working unit.

4. A suturing and ligating method according to claim 1, wherein the rotary input unit is manually elastically rotatable clockwise and counterclockwise from an initial position, wherein the rolling mechanism is capable of rolling the first opening and closing mechanism in response to manual rotation of the rotary input unit.

5. A suturing and ligating method according to claim 1, wherein the winding step further comprises the step of turning the proximal end portion with the rolling mechanism through an angle ranging from 90° to 200°.

6. A suturing and ligating method according to claim 1, wherein the winding step, the suture strand gripping step and the pulling step are carried out at least two times.

7. A suturing and ligating method according to claim 1, wherein the winding step, the suture strand gripping step and the pulling step are carried out two times, wherein the suture strand is wound around the second distal-end working unit once in one direction in the first winding step, and once in the direction opposite to the one direction in the second winding step, so as to form a square knot, and between the second pulling step and the tightening step, the suturing and ligating method comprises:

a slip knot creating step of opening the first opening and closing mechanism to release the needle, gripping a portion of the suture strand, which is not inserted into the tissue, at a point of the suture strand closer to the tissue than the square knot, and pulling the first distal-end working unit and the second distal-end working unit in opposite directions so that the suture strand between the first distal-end working unit and the second distal-end working unit becomes straight, thereby creating a slip knot; and a sliding step of sliding the slip knot to the tissue by the first opening and closing mechanism.

8. A suturing and ligating method according to claim 7, wherein the first opening and closing mechanism comprises a groove in a opening and closing surface thereof, and the groove forms a hole for allowing the suture strand to extend therethrough when the first opening and closing mechanism is closed, and the sliding step comprises the steps of opening the first opening and closing mechanism to release the suture strand, then closing the first opening and closing mechanism such that the suture strand, which is not inserted into the tissue, extends through the hole at a point of the suture strand closer to a portion gripped by the second opening and closing mechanism than the slip knot, and moving the first opening and closing mechanism to slide the slip knot.

* * * * *